US007151169B2

(12) United States Patent
Thompson et al.

(10) Patent No.: US 7,151,169 B2
(45) Date of Patent: Dec. 19, 2006

(54) SPECIFIC BINDING MEMBERS FOR TGFβ$_1$

(75) Inventors: Julia Elizabeth Thompson, Cambridgeshire (GB); Simon Nicholas Lennard, Suffolk (GB); Alison Jane Wilton, Cambridge (GB); Peta Sally Helena Braddock, Huntingdon (GB); Sarah Leila Du Fou, Herfordshire (GB); John Gerald McCafferty, Cambridgeshire (GB); Louise Anne Conroy, Cambridge (GB); Philip Ronald Tempest, Cambridgeshire (GB)

(73) Assignee: Cambridge Antibody Technology Limited (GB)

( * ) Notice: Subject to any disclaimer, the term of this patent is extended or adjusted under 35 U.S.C. 154(b) by 531 days.

(21) Appl. No.: 10/243,308

(22) Filed: Sep. 13, 2002

(65) Prior Publication Data
US 2003/0064069 A1 Apr. 3, 2003

Related U.S. Application Data

(62) Division of application No. 09/560,198, filed on Apr. 28, 2000, now Pat. No. 6,492,497.

(60) Provisional application No. 60/131,983, filed on Apr. 30, 1999.

(51) Int. Cl.
C12N 15/11 (2006.01)

(52) U.S. Cl. ............... 536/23.1; 536/23.5; 530/388.85; 530/387.1; 530/388.15; 424/124.1; 424/156.1; 424/133.1; 424/155.1; 424/130.1

(58) Field of Classification Search ............... 536/23.1, 536/23.5; 530/388.85, 387.1, 388.15; 424/142.1, 424/156.1, 133.1, 155.1, 130.1
See application file for complete search history.

(56) References Cited

U.S. PATENT DOCUMENTS

| 4,634,666 | A | 1/1987 | Engleman et al. |
|---|---|---|---|
| 4,816,397 | A | 3/1989 | Boss et al. |
| 4,946,778 | A | 8/1990 | Ladner et al. |
| 5,091,513 | A | 2/1992 | Huston et al. |
| 5,223,409 | A | 6/1993 | Ladner et al. |
| 5,262,319 | A | 11/1993 | Iwata et al. |
| 5,395,750 | A | 3/1995 | Dillon et al. |
| 5,571,714 | A | 11/1996 | Dasch et al. |
| 5,585,089 | A | 12/1996 | Queen et al. |
| 5,614,367 | A | 3/1997 | Kaluza et al. |
| 5,616,561 | A | 4/1997 | Barcellos-Hoff |
| 5,662,904 | A | 9/1997 | Ferguson et al. |
| 5,688,504 | A | 11/1997 | Morgan, Jr. |
| 5,739,277 | A | 4/1998 | Presta et al. |
| 5,772,998 | A | 6/1998 | Dasch et al. |
| 5,783,181 | A | 7/1998 | Browne et al. |
| 5,783,185 | A | 7/1998 | Dasch et al. |
| 5,824,297 | A | 10/1998 | Iwata et al. |
| 5,871,724 | A | 2/1999 | Iwata et al. |
| 5,885,793 | A | 3/1999 | Griffiths et al. |
| 6,090,383 | A | 7/2000 | Dasch et al. |
| 6,248,516 | B1 | 6/2001 | Winter et al. |
| 6,331,415 | B1 | 12/2001 | Cabilly et al. |
| 6,419,928 | B1 | 7/2002 | Dasch et al. |
| 2005/0049403 | A1* | 3/2005 | Thompson et al. .... 530/388.25 |

FOREIGN PATENT DOCUMENTS

| AU | B-27617/88 | 7/1989 |
|---|---|---|
| EP | A 0120694 | 10/1984 |
| EP | A 0125023 | 11/1984 |
| EP | A 184187 | 6/1986 |
| EP | A 239400 | 9/1987 |
| EP | 0324162 | 12/1988 |
| EP | 0368684 | 3/1994 |
| GB | 2188638 | 10/1987 |
| GB | 2 288 118 A | 10/1995 |
| GB | 2 305 921 | 4/1997 |
| JP | 06165692 | 6/1994 |
| JP | 06165692 A | 6/1994 |
| WO | WO 88/06630 | 9/1988 |
| WO | WO 88/09344 | 12/1988 |
| WO | WO 90/02809 | 3/1990 |
| WO | WO 90/05144 | 5/1990 |
| WO | WO 90/14424 | 11/1990 |
| WO | WO 90/14430 | 11/1990 |
| WO | WO 90/14443 | 11/1990 |
| WO | WO 91/04748 | 4/1991 |
| WO | WO 91/09967 | 7/1991 |
| WO | WO 91/10737 | 7/1991 |
| WO | WO 91/17271 | 11/1991 |
| WO | WO 92/00330 | 1/1992 |
| WO | WO 92/01047 | 1/1992 |
| WO | WO 92/06204 | 4/1992 |
| WO | WO 92/09690 | 6/1992 |
| WO | WO 92/17206 | 10/1992 |
| WO | WO 92/18619 | 10/1992 |

(Continued)

OTHER PUBLICATIONS

Rudikoff et al (Proc Natl Acad Sci USA 1982 vol. 79 p. 1979).*
Supplemental Search Report of Corresponding European Application No. 04014972.6, dated Dec. 12, 2004.
Burmester, James K., et al., "Mutational Analysis of a Transforming Growth Factor-β Receptor Binding Site," *Growth Factors, Harwood Academic Publishers*, vol. 15, No. 3, 1998, pp. 231-242.

(Continued)

Primary Examiner—Larry R. Helms
Assistant Examiner—Parithosh K. Tungaturthi
(74) Attorney, Agent, or Firm—Howrey LLP; David W. Clough

(57) ABSTRACT

The invention provides specific binding members, for example in the form of antibody variable domains, based on the CDR3 sequences of the antibody VH regions of SL15 (SEQ ID NO:4) and JT182 (SEQ ID NO:10). The antibodies have strong neutralising activity for TGFβ$_1$ and are useful in treating conditions associated with excess TGFβ$_1$ activity, such as fibrosis, immune responses and tumor progression.

9 Claims, 11 Drawing Sheets

FOREIGN PATENT DOCUMENTS

| | | |
|---|---|---|
| WO | WO 92/20791 | 11/1992 |
| WO | WO 93/06213 | 4/1993 |
| WO | WO 93/11161 | 6/1993 |
| WO | WO 93/11236 | 6/1993 |
| WO | WO 93/14782 | 8/1993 |
| WO | WO 93/17708 | 9/1993 |
| WO | WO 93/19783 | 10/1993 |
| WO | WO 93/21945 | 11/1993 |
| WO | WO 94/13804 | 6/1994 |
| WO | WO 94/18227 | 8/1994 |
| WO | WO 95/13827 | 5/1995 |
| WO | WO 97/13844 | 4/1997 |

OTHER PUBLICATIONS

Flanders, Kathleen, C., et al., "Antibodies to Peptide Determinants in Transforming Growth Factor β and Their Applications," *Biochemistry, American Chemical Society*, 1988, vol. 27, 739-746.

Hoefer, Magdalene, et al., "Anti-Transforming Growth Factorβ) Antibodies With Predefined Specificity Inhibit Metastasis of Highly Tumorigenic Human Xenotransplants in nu/nu Mice," *Cancer Immunology and Immunotherapy*, vol. 41, No. 5, 1995, 302-308.

Su Wen Qian, et al., "Binding Affinity of Transforming Growth Factor-Beta for its Type II Receptor is Determined by the C-Terminal Region of the Molecule," *Journal of Biological Chemistry, American Society of Biological Chemists*, vol. 271, No. 48, Nov. 29, 1996, 30656-30662.

R&D Systems Inc. Catalog, "Monoclonal Anti-human TGF-β1 Antibody", Catalog No. MAG240, Jun. 20, 2000, pp. 1-2.

Oncogene Research Products, Transforming Growth Factorβ1 (Ab-1) Monoclonal Antibody, Catalog No. GF33L.

R&D Systems, Inc. Catalog, Monoclonal Anti-human TGF-β1 Antibody, Catalog No. MAB2401, Jan. 30, 2002, pp. 1-2.

R&D Systems, Inc. Catalog, Monoclonal Anti-TGF-β2 Antibody, Catalog No. MAB612, Jun. 28, 2001, pp. 1-2.

R&D Systems, Inc. Catalog, Monoclonal Anti-TGF-β3 Antibody, Catalog No. MAB243, Nov. 15, 2000, pp. 1-2.

R&D Systems, Inc. Catalog, Monoclonal Anti-TGF-β3 Antibody, Catalog No. MAB643, Jun. 21, 2001, pp. 1-2.

Data Specification Sheet—Chemicon International, Catalog No. MAB1032, "Mouse Anti-Human Transforming Growth Factorβ (TGFβ) Monoclonal Antibody."

Yes Biotech Laboratories, Ltd. Website homepage—http://www.yesbiotech.com/index.html.

Monoclonal Antibodies: Murine Anti-Human TGFβ data sheet—Thursday, Feb. 7, 2002, Yes Biotech Laboratories Ltd. Website: http://www.yesbiotech.com/tech14.htm.

RDI—Research Diagnostics, Inc. Website homepage—Thursday, Feb. 7, 2002; Quick Access to Links for On Line Spec Sheets—http://www.researchd.com/index.htm.

Cytokines, Growth Factors Chemokines: Antibodies: and Mouse Monoclonal Antibody to Human TFG-β (Oct. 3, 2001)—RDI—Research Diagnostics, Inc. Website homepage—Thursday, Feb. 7, 2002; Links for On Line Spec Sheets—http://www.researchd.com/cytokines/lgfbab.htm.

Catalog No. M700022, Mouse Anti-Human TGFβ(2C5); Antigenix America, Inc.; http://www.SciQuest.com/cgi-bin/ncommerce3/ExecMacro/product_details.d2w/report?Tmstmp=1013101956096&Refresh=N, Thursday, Feb. 7, 2002.

Catalog No. MO-C40009.D, Mouse Anti-Human TGFβMonoclonal Antibody, Clone No. 2C6; Anogen/Yes Biotech Laboratories Ltd.; http://www.SciQuest.com/cgi-bin/ncommerce3/ExecMacro/product_details.d2w/report?Tmstmp=1013102046067&; Thursday, Feb. 7, 2002.

Catalog No. MO-C40009.E, Mouse Anti-Human TGFβ Monoclonal Antibody, Clone No. 2E6; Anogen/Yes Biotech Laboratories Ltd.; http://www.SciQuest.com/cgi-bin/ncommerce3/ExecMacro/product_details.d2w/report?Tmstmp=1013102046067&; Thursday, Feb. 7, 2002.

Catalog No. MO-C40009.F, Mouse Anti-Human TGFβ Monoclonal Antibody, Clone No. 8C4; Anogen/Yes Biotech Laboratories Ltd.; http://www.SciQuest.com/cgi-bin/ncommerce3/ExecMacro/product_details.d2w/report?Tmstmp=1013102046067&; Thursday, Feb. 7, 2002.

Catalog No. MO-C40009.H, Mouse Anti-Human TGFβ Monoclonal Antibody, Clone No. 4C2; Anogen/Yes Biotech Laboratories Ltd.; http://www.SciQuest.com/cgi-bin/ncommerce3/ExecMacro/product_details.d2w/report?Tmstmp=1013102046067&; Thursday, Feb. 7, 2002.

Oncogene Research Products website—Catalog No. GF16—Transforming Grwoth Factorβ3 (Ab-1) Monoclonal Antibody, http://www.apoptosis.com/products/ProductDetail_ONC.asp?catNO=GF16, Feb. 7, 2002.

ATCC, Welcome to the Monoclonal Connection (Hybridoma Data Bank)—What is the Hybridoma Data Bank (HDB), http:/www/atcc:org/SearchCatalogs/hdbcfm, pp. 1-2, Feb. 7, 2002.

ATCC Search "TGFb" Catalog No. 1024236 Re: 1 G>*Homo sapiens* 1, CN>human an 1024236—http://phage.atcc.org/cgi-bin/searchengine/hdb/Longview.cgl?view=/pub/textfiles/hdb-di.out. 17906760&text=TGFb, Feb. 7, 2002.

ATCC Search "TGFb"Catalog No. 1024691 Re: 1 G>*Homo sapiens* 1, CN>human an 1024691—http://phage.atcc.org/cgi-bin/searchengine/hdb/Longview.cgl?view=/pub/textfiles/hdb-di.out. 17906760&text=TGFb, Feb. 7, 2002.

Abstract, Dasch, J. R., et al., "Monoclonal antibodies recognizing transforming growth factor-beta.Bioactivity neutralization and transforming growth factor beta 2 affinity purification," *J. Immunol.*, Mar. 1, 1989:142(5):1536-41.

Abstract, Lucas, C., et al., The autocrine production of transforming growth factor-beta 1 during lymphocyte activation. A study with a monoclonal antibody-based ELISA, *J. Immunol.*, Sep. 1, 1990:145(5):1415-22.

Abstract, Wojtowicz-Praga, S., et al., "Modulation of B16 melanoma growth and metastasis by anti-transforming growth factor beta antibody and interleukin-2," *J. Immunother. Emphasis Tumor Immunol.*, May 1996; 19(3):169-75.

Abstract, Hoefer, M., et al., "Anti-(transforming growth factor beta) antibodies with predefined specificity inhibit metastasis of highly tumorigenic human xenotransplants in nu/nu mice," *Cancer Immunol. Immunother.*, Nov. 1995 41(5):302-8.

Abstract, Tahara N., et al., "Synthetic peptide-generated monoclonal antibodies to transforming growth factor-beta1," *Hybridoma*, 12(4):441-53, Aug. 1993.

Lucas, Catherine, et al., "The Autocrine Production of Transforming Growth—Factorβ₁ During Lymphocyte Activation," *The Journal of Immunology*, vol. 145, 1415-1422, No. 5, Sep. 1, 1990.

Tahara, N., et al., "Synthetic Peptide-Generated Monoclonal Antibodies to Transforming Growth Factor-β1," Hybridoma, vol. 12, No. 4, 1993, 441-453.

Hoefer, Magdalene, et al., "Anti-(transforming growth factor β) antibodies with predefined specificity inhibit metastasis of highly tumorigenic human xenotransplants in nu/nu mice," *Cancer Immunol. Immunother.*, (1995) 41:302-308.

Rudikoff, et al., Proc., Natl. Acad. Sci. UsA 79:1979, 1982.

Arteaga et al., "Transforming Growth Factor .beta..sub.1 Can Induce Estrogen-Independent Tumorigenicity of Human Breast Cancer Cells in Athymic Mice", Cell Growth and Differentiation, 4(3):193-201 (1993).

Arteaga et al., "Anti-Transforming Growth Factor (TGF)-.beta. Antibodies Inhibit Breast Cancer Cell Tumorigenicity and Increase Mouse Spleen Natural Killer Cell Activity", J. Clin. Invest., 92(6):2569-2576 (1993).

Awadh et al., "Airway wall thickness in patients with near fatal asthma and control groups: assessment with high resolution computed tomographic scanning", Thorax, 53(4):248-253 (1998).

Bagshawe et al., "Antibody-Enzyme Conjugates Can Generate Cytotoxic Drugs from Inactive Precursors at Tumor Sites", Antibody, Immunoconjugates and Radiopharmaceuticals, 4:915-922 (1991).

Barbas et al., "In vitro evolution of a neutralizing human antibody to human immunodeficiency virus type 1 to enhance affinity and broaden strain cross-reactivity", Proc. Nat'l. Acad. Sci., USA, 91:3809-3813 (1994).

Bebbington et al., "High-Level Expression of a Recombinant Antibody from Myeloma Cells Using a a Glutamine Synthetase Gene as an Amplifiable Selectable Marker", Bio/Technology10:169-175 (1992).

Bird et al., "Single-Chain Antigen-Binding Proteins", Science, 242:423-426 (1988).

Blanckaert et al., "Differential Growth Factor Production, Secretion, and Response by High and Low Metastatic Variants of B16BL6 Melanoma.sup.1", Cancer Res., 53(17):4075-81 (1993).

Border et al., "Suppression of experimental glomerulonephritis by antiserum against transforming growth factor .beta.1", Nature, 346:371-374 (1990).

Brewster et al., "Myofibroblasts and Subepithelial Fibrosis in Bronchial Asthma", Am. J. Respir. Cell Mol. Biol., 3(5):507-511 (1990).

Burmester et al., "Mutational Analysis of a Transforming Growth Factor-.beta. Receptor Binding Site", Growth Factors, 15:231-242 (1998).

Carroll et al., "The Structure of Large and Small Airways in Nonfatal and Fatal Asthma", Am. Rev. Respir. Dis., 147(2):405-410 (1993).

Dasch et al., "Monoclonal Antibodies Recognizing Transforming Growth Factor-.beta." (Bioactivity Neutralization and Transforming Growth Factor .beta.2 Affinity Purification), J. Immunol., 142:1536-1541 (1989).

Demoly et al., "Cell Proliferation in the Bronchial Mucosa of Asthmatics and Chronic Bronchitics", Am. J. Respir. Crit. Care Med., 150(1):214-217 (1994).

Donovan et al., "TGF.beta.-1 Regulation of VEGF Production by Breast Cancer Cells", Ann. Surg. Oncol., 4(8):621-627 (1997).

Flanders et al., "Localization and actions of transforming growth factor-.beta.s in the embryonic nervous system", Development, 113:183-191 (1991).

Folkman, "The influence of angiogenesis research on management of patients with breast cancer", Breast Cancer Res. Treat., 36(2):109-118 (1995).

Foreman et al., "A Simple Organ Culture Model for Assessing the Effects of Growth Factors on Corneal Re-epithelialization", Exp. Eye Res., 62:555-564 (1996).

Giri et al., "Effect of antibody to transforming growth factor .beta. on bleomycin induced accumulation of lung collagen in mice", Thorax, 48:959-966 (1993).

Gizycki et al., "Myofibroblast Involvement in the Allergen-induced Late Response in Mild Atopic Asthma", Am. J. Respir. Cell Mol. Biol., 16(6):664-673 (1997).

Gram et al., "In vitro selection and affinity maturation of antibodies from a naive combinatorial immunoglobulin library", Proc. Nat'l. Acad. Sci., USA, 89:3576-3580 (1992).

Gridley et al., "Effects of Anti-transforming Growth Factor-.beta. Antibody and Interleukin-2 in Tumor-bearing Mice", Cancer Biother., 8(2):159-170 (1993).

Harmey et al., "Regulation of Macrophage Production of Vascular Endothelial Growth Factor (VEGF) by Hypoxia and Transforming Growth Factor .beta.-1", Am. Surg. Oncol., 5(3):271-278 (1998).

Hata et al., "TGF-.beta. signaling and cancer: structural and functional consequences of mutations in Smads", Mol. Med. Today, 4(6):257-262 (1998).

Hoefer and Anderer, "Anti-(transforming growth factor .beta. antibodies with predefined specificity inhibit metastasis of highly tumorigenic human xenotransplants in nu/nu mice", Cancer Immunol. Immunother., 41(5):302-308 (1995).

Hojo et al., "Cyclosporine induces cancer progression by a cell-autonomous mechanism", Nature, 397:530-534 (1999).

Holliger et al., "Engineering bispecific antibodies", Current Opinion Biotechnol., 4:446-449 (1993).

Holliger et al., "Diabodies": Small bivalent and bispecific antibody fragments, Proc. Nat'l. Acad. Sci. USA, 90:6444-6448 (1993).

Hu et al., "Minibody: A Novel Engineered Anti-Carcinoembryonic Antigen Antibody Fragment (Single-Chain Fv-C.sub.h 3) Which Exhibits Rapid, High-Level Targeting of Xenografts.sup.1", Cancer Res., 56:3055-3061 (1996).

Huston et al., "Protein engineering of antibody binding sites: Recovery of specific antivity in an anti-digoxin single-chain Fv analogue produced in *Escherrichia coli*", Proc. Nat'l. Acad. Sci., USA, 85:5879-5883 (1988).

Laitinen et al., "Damage of the Airway Epithelium and Bronchial Reactivity in Patients with Asthma .sup.1-3", Am. Rev. Respir. Dis., 131(4):599-606 (1985).

Lange et al., "A 15-Year Follow-Up Study of Ventilatory Function in Adults with Asthma.sup.1-3", N. Engl. J. Med., 339(17):1194-1200 (1998).

Ledermann et al., "A Phase-I Study Of Repeated Therapy with Radiolabelled Antibody to Carcinoembryonic Antigen Using Intermittent or Continuous Administration of Cyclosporin A to Suppress the Immune Response", Int. J. Cancer, 47:659-664 (1991).

Logan et al., "Effects of Transforming Growth Factor .beta..sub.1 on Scar Production in the Injured Central Nervous System of the Rat", Eur. J. Neurosci., 6:355-363 (1994).

Lucas et al., "[29] Generation of Antibodies and Assays for Transforming Growth Factor 62", Meth. in Enzymology, 198:303-316 (1991).

Lucas et al., "The Autocrine Production of Transforming Growth Factor—.beta..sub.1 During Lymphocyte Activation", The Journal of Immunology, 145:1415-1422 (1990).

Lundgren R., et al., "Morphological studies of bronchial mucosal biopsies from asthmatics before and after ten years of treatment with inhaled steroids", Eur. Respir. J., 1(10):883-889 (1988).

Mao et al., "Immunotherapy with Low-dose Interleukin-2 and Anti-transforming Growth Factor-.beta. Antibody in a Murine Tumor Model", Cancer Biother., 9(4):317-327 (1994).

Markowitz et al., "Inactivation of the Type II TGF-.beta. Receptor in Colon Cancer Cells with Microsatellite Instability", Science, 268(5215):1336-1338 (1995).

Marks et al., "By-Passing Immunization: Building High Affinity Human Antibodies by Chain Shuffling", Bio/Technology, 10:779-783 (1992).

Merwin et al., "Vascular Cells Respond Differentially to Transforming Growth Factors .beta..sub.1 and B.sub.2 In Vitro", Am. J. Pathol., 138:37-51 (1991).

Orlandi et al., "Cloning immunoglobulin variable domains for expression by the polymerase chain reaction", Proc. Nat'l. Acad. Sci. USA, 86:3833-3837 (1989).

Ottmann & Pelus, "Differential Proliferative Effects of Transforming Growth Factor-.beta.on Human Hematopoietic Progenitor Cells. sup.1", J. Immunol., 140:2661-2665 (1988).

Larrick et al. "Recombinant antibodies", Hum. Antibody. Hybridomas, 2: 172-89 (1991).

Avrameas, "Natural autoantibodies: from 'horror autotoxicus' to 'gnothi seauton'," *Immunology Today* 12:154-159 (1991).

Barbas et al., "High-affinity self-reactive human antibodies by design and selection: Targeting the integrin ligand binding site," *Proc. Natl. Acad. Sci., USA, 90*:10003-10007 (1993).

Bass et al., "Hormone Phage: An Enrichment Method for Variant Proteins With Altered Binding Properties," *Proteins, Structure, Function and Genetics* 8:309-314 (1990).

Bendtzen et al., "Autoantibodies to cytokines—friends or foes?," *Immunology Today* 11(5):167-169 (1990).

Bouanani, M. et al, "Autoimmunity to Human Thyroglobulin," *Arthritis and Rheumatism*, 34(12):1585-1593 (Dec. 1991).

Brown et al., "Physicochemical Activation of Recombinant Latent Transforming Growth Factor-beta's 1, 2, and 3," *Growth Factors*, 3:35-43 (1990).

Bye et al., "Germline Variable of Gene Segment Derivation of Human Monoclonal Anti-Rh(D) Antibodies," *J. Clin. Invest.*, 90(6):2481-2490 (Dec. 1992).

Conner et al., "Correlation of Fibrosis and Transforming Growth Factor-β Type 2 Levels in the Eye," *J. Clin. Invest.*, 83:1661-1666 (1989).

Danielpour et al., "Immunodetection and Quantitation of the Two Forms of Transforming Growth Factor-Beta (TGF-β1 and TGF-β2) Secreted by Cells in Culture," *J. Cellular Physiology*, 138:79-86 (1989).

Danielpour et al., "Sandwich Enzyme-Linked Immunosorbent Assays (SELISAs) Quantitate and Distinguish Two Forms of Transforming Growth Factor-Beta (TGF-β1 and TGF-β2) in Complex Biological Fluids," *Growth Factors*, 2:61-71 (1989).

Daopin et al., "Crystal Structure of TGF-β2 Refined at 1.8 Å Resolution," *Proteins: Structure, Function and Genetics*, 17:176-192 (1993).

de la Cruz et al., Immumogenicity and Epitope Mapping of Foreign Sequences via Genetically Engineered Filamentous Phage, *J. Biol. Chem.* 263(9):4318-4322 (1988).

Derynck et al., "The Murine Transforming Growth Factor-β Precursor," *J. Biological Chemistry*, 261:4377-4379 (1986).

Ditzel et al., "The nature of the autoimmune antibody repertoire in human immunodeficiency virus type 1 infection," *Proc. Natl. Acad. Sci. USA* 91:3710-3714 (1994).

Erlebacher et al., "Increased Expression of TGF-β2 in Osteoblasts Results in an Osteoporosis-like Phenotype," *J. Cell Biology*, 132:195-210 (1996).

Fisch, I. et al., "A strategy of exon shuffling for making large peptide repertoires displayed on filamentous bacteriophage," *Proc. Natl. Acad. Sci., USA*, 93:7761-7766 (Jul. 1996).

Flanders et al., "Antibodies to Peptide Determinants in Transforming Growth Factor β and Their Applications," *Biochemistry*, 27:739-746 (1988).

Flanders et al., "Antibodies to Transforming Growth Factor-β2 Peptides: Specific Detection of TGF-β2 in Immunoassays," *Growth Factors*, 3:45-52 (1990).

Griffiths, A.D. et al., "Human anti-self antibodies with high specificity from phage display libraries," *EMBO J.*, 12(2):725-734 (1993).

Griffiths, A.D. et al., "Isolation of High Affinity Human Antibodies Directly from Large Synthetic Repertoires," *EMBO J.* 13(14):3245-3260 (1994).

Griffiths et al., "Three-dimensional structure of recombinant human osteogenic protein 1: Structural paradigm for the transforming growth factor β superfamily," *Proc. Natl. Acad. Sci., USA*, 93:878-883 (1996).

Hassan et al., "Prevalance of anti-Fab antibodies in patients with autoimmune and infectious diseases," *Clin. exp. Immunol.* 89:423-426 (1992).

Ikeda et al., "Human Transforming Growth Factor Type β2: Production by a Prostatic Adenocarcinoma Cell Line, Purification, and Initial Characterization," *Biochemistry*, 26:2406-2410 (1987).

International Search Report; International Application No. PCT/GB92/02240.

James, K. and Bell, G.T., "Human monoclonal antibody production: Current status and future prospects," *Journal of Immunological Methods*, 100:5-40 (1987).

Jampel et al., "Transforming growth Factor-β in human aqueous humor," *Current Eye Research*, 9:963-969 (1990).

Jerome et al., "Adenocarcinoma Reactive Cytotoxic T Lymphocytes Recognize an Epitope Present on the Protein Core of Epithelial Mucin Molecules," *Cellular Immunity and the Immunotherapy of Cancer*, pp. 321-328 (1990).

Kang et al., "Linkage of recognition and replication functions by assembling combinatorial antibody Fab libraries along phage surface," *Proc. Natl. Acad. Sci. USA* 88:4363-4366 (1991).

Karlsson et al., "Kinetic analysis of monoclonal antibody-antigen interactions with a new biosensor based analytical system," *J. Immunological Methods*, 145:229-240 (1991).

Kaufman, R.J., "Selection and Coamplification of Heterologous Genes in Mammalian Cells," *Methods Enzymology*, 185:537-566 (1990).

Khaw et al., "Activation and Suppression of Fibroblast Function," *Eye*, 8:188-195 (1994).

Kim, J.G. and Abeyounis, C.J., "Monoclonal Rat Antibodies to Rat Carcinoembryonic Antigen," *Immunological Investigations*, 17(1):41-48 (1988).

Kim, J.G. and Abeyounis, C.J., "Isolation and Characterization of Rat Carcinoembryonic Antigen," *Int. Arch. Allergy Appl. Immunol.*, 92:43-49 (1990).

Kvanta, A., "Expression and Secretion of Transforming Growth Factor-β in Transformed and Nontransformed Retinal Pigment Epithelial Cells," *Opthalmic Res.*, 26:361-367 (1994).

Leusch et al., "Failure to demonstrate TNF α-specific autoantibodies in human sera by ELISA and Western blot," *Journal of Immunological Methods* 139:145-147 (1991).

Logan et al., "Enhanced expression of transforming growth factor β1 in the rat brain after a localized cerebral injury," *Brain Research*, 587:p. 216-225 (1992).

Marks J.D. et al., "By-passing Immunization Human Antibodies from V-gene Libraries Displayed on Phage," *J. Molecular Biology*, 222:581-597 (1991).

Massagué et al., "The Transforming Growth Factor-β Family," *Annual Rev. Cell Biol.*, 6:597-641 (1990).

McCafferty et al., "Phage antibodies: filamentous phage displaying antibody variable domains," *Nature* 348:552-554 (1990).

McCafferty et al., "Selection and Rapid Purification of Murine Antibody Fragments That Bind a Transition-State Analog by Phage Display," *Appl. Biochem. Biotech.*, 47:157-173 (1994).

Merwin et al., "Vascular Cells Respond Differentially to Transforming Growth Factors Beta$_1$ and Beta$_2$ In Vitro," *American J. Pathology*, 138:37-51 (1991).

Milstein, F.R.S., "Antibodies: a paradigm for the biology of molecular recognition," *Proc. R. Soc. London* B 239:1-16 (1990).

Moynier et al., "The B Cell Repertoire in Rheumatoid Arthritis. I. Frequency of EBV-Inducible Circulating Precursors Producing Autoantibodies," *Journal of Autoimmunity* 4:631-649 (1991).

Munro S. et al., "An Hsp70-like Protein in the ER: Identity with the 78 kd Glucose-Regulated Protein and Immunoglobulin Heavy Chain Binding Protein," *Cell*, 46:291-300 (Jul. 1986).

Nissim et al., "Antibody fragments from a 'single pot' phage display library as immunochemical reagents," *EMBO J.*, 13:692-698 (1994).

Nossal, G.J., "Immunologic Tolerance: Collaboration Between Antigen and Lymphokines," *Science*, 245:147-153 (1989).

Parmley and Smith, "Antibody-selectable filamentous fd phage vectors: affinity purification of target genes," *Gene* 73:305-318 (1988).

Pena et al., "Effects of TGF-β and TGF-β Neutralizing Antibodies on Fibroblast-Induced Collagen Gel Contraction: Implications for Proliferative Vitreoretinopathy," *Investigative Opthalmology Visual Science*, 35:2804-2808 (1994).

Pfeffer et al., "Transforming Growth Factor Beta 2 is the Predominant Isoform in the Neural Retina, Retinal Pigment Epithelium-Choroid and Vitreous of the Monkey Eye," *Exp. Eye Res.*, 59:323-333 (1994).

Pircher et al., "β-Transforming Growth Factor Is Stored in Human Blood Platelets as a Latent High Molecular Weight Complex," *Biochemical Biophysical Research Communications*, 136(1):30-37 (1986).

Plückthun, A., "Antibody Engineering: Advances From the Use of *Escherichia coli* Expression Systems," *Bio/Technology*, 9:545-551 (Jun. 1991).

Portolano, S. et al., "A Human Fab Fragment Specific for Thyroid Peroxidase Generated by Cloning Thyroid Lymphocyte-Derived Immunoglobulin Genes in a Bacteriophage Lambda Library," *Biochemical and Biophysical Research Communications*, 179(1):372-377 (Aug. 30, 1991).

Qian et al., "Binding Affinity of Transforming Growth Factor-β for Its Type II Receptor Is Determined by the C-terminal Region of the Molecule," *J. Biological Chemistry*, 271:30656-30662 (1996).

Randall et al., "A novel, sensitive bioassay for transforming growth factor β," *J. Immunological Methods*, 164:61-67 (1993).

Reff, M.E., "High-level production of recombinant immunoglobulins in mammalian cells," *Current Opinion in Biotechnology*, 4:573-576 (1993).

Reiter et al., "Engineering antibody Fv fragments for cancer detection and therapy: Disulfide-stablized Fv fragments," *Nature Biotechnology*, 14:1239-1245 (1996).

Ridgeway et al., "'Knos-into-holes' engineering of antibody $C_H3$ domain for heavy chain heterodimerization," *Protein Engineering*, 9:616-621 (1996).

Roberts et al., "Mesoderm Induction in *Xenopus laevis* Distinguishes Between the Various TGF-β Isoforms," *Growth Factors*, 3:277-286 (1990).

Roberts et al., "The Transforming Growth Factor-βs," in *Handbook of Experimental Pharmacology*, Eds. M.13 Sporn et al., Springer Heideberg, pp. 419-472 (1990).

Sanz et al., "Nucleotide Sequences of Eight Human Natural Autoantibody $V_H$ Regions Reveals Apparent Restricted Use of $V_H$ Families," *The Journal of Immunology* 142(11):4054-4061 (1989).

Schier et al., "Isolation of Picomolar Affinity Anti-c-erbB-2 Single-chain Fv by Molecular Evolution of the Complementarity Determining Regions in the Center of the Antibody Binding Site," *J. Mol. Biol.*, 263:551-567 (1996).

Schlunegger et al., "An Unusual Feature Revealed by the Crystal Structure at 2.2Å Resolution of Human Transforming Growth Factor-β2," *Nature*, 358:430-434 (1992).

Sekigawa et al., "Characterization of Autoantibodies to the CD4 Molecule in Human Immunodeficiency Virus Infection," *Clinical Immunology and Immunopathology* 58:145-153 (1991).

Shah et al., "Control of scarring in adult wounds by neutralising antibody to transforming growth factor β," *Lancet*, 339:213-214 (1992).

Shah, et al., "Neutralising antibody to TGF-$β_{1,2}$ reduces cutaneous scarring in adult rodents," *J. Cell Science*, 107:1137-1157 (1994).

Shah, M. et al., "Neutralisation of TGF-$β_1$ and TGF-$B_2$ or exogenous addition of TGF-$β_3$ to cutaneous rat wounds reduces scarring," *J. Cell Science*, 108:985-1002 (1995).

Short et al., "λ ZAP: a bacteriophage λ expression vector with *in vivo* excision properties," *Nucleic Acids Research* 16(15):7583-7600 (1988).

Smith, "Filamentous Fusion Phage: Novel Expression Vectors That Display Cloned Antigens on the Virion Surface," *Science* 228:1315-1317 (1985).

Stemmer et al., "Rapid evolution of a protein in vitro by DNA shuffling," *Nature*, 370:389-391 (1994).

Suardet et al., "Responsiveness of Three Newly Established Human Colorectal Cancer Cell Lines to Transforming Growth Factors $β_1$ and $β_2$," *Cancer Research*, 52:3705-3712 (1992).

Tahara et al., "Synthetic Peptide-Generated Monoclonal Antibodies to Transforming Growth Factor-$β_1$," *Hybridoma*, 12(4):441-453 (1993).

Traunecker, A. et al., "Bispecific single chain molecules (Janusins) target cytotoxic lymphocytes on HIV infected cells," *EMBO J.*, 10(12):3655-3659 (1991).

Trill, J.J. et al., "Production of monoclonal antibodies in COS and CHO cells," *Current Opinion in Biotechnology*, 6:553-560 (1995).

Tsunetsugu-Yokota et al., "Expression of an immunogenic region of HIV by a filamentous bacteriophage vector," *Gene* 99:261-265 (1991).

Wahl et al., "Reversal of Acute and Chronic Synovial Inflammation by Anti-Transforming Growth Factor β," *J. Experimental Medicine*, 177:225-230 (1993).

Wakefield et al., "Recombinant TGF-$β_1$ Is Synthesized as a Two-Component Latent Complex That Shares Some Structural Features with the Native Platelet Latent TGF-$β_1$ Complex," *Growth Factors*, 1:203-218 (1989).

Ward, E.S. et al., "Binding activities of a repertoire of single immunoglobulin variable domains secreted from *Escherichia coli*," *Nature*, 341:544-546 (Oct. 12, 1989).

Winter, G. et al., "Man-made antibodies," *Nature*, 349:293-299 (Jan. 24, 1991).

Wolf et al., "Antibodies against Transforming Growth Factor-$β_1$ Suppress Intimal Hyperplasia in a Rat Model," *J. Clin. Invest.*, 93:1172-1178 (1994).

Yativ et al., "The Detection of Antithyroglobulin Activity in human Serum Monoclonal Immunoglobulins (Monoclonal Gammopathies)," *Immunol. Res.* 12:330-337 (1993).

Derynck et al., "A new type of transforming growth factor-beta, TGF-beta 3." EMBO J. Dec. 1, 1988; 7(12): 3737 -43.

* cited by examiner

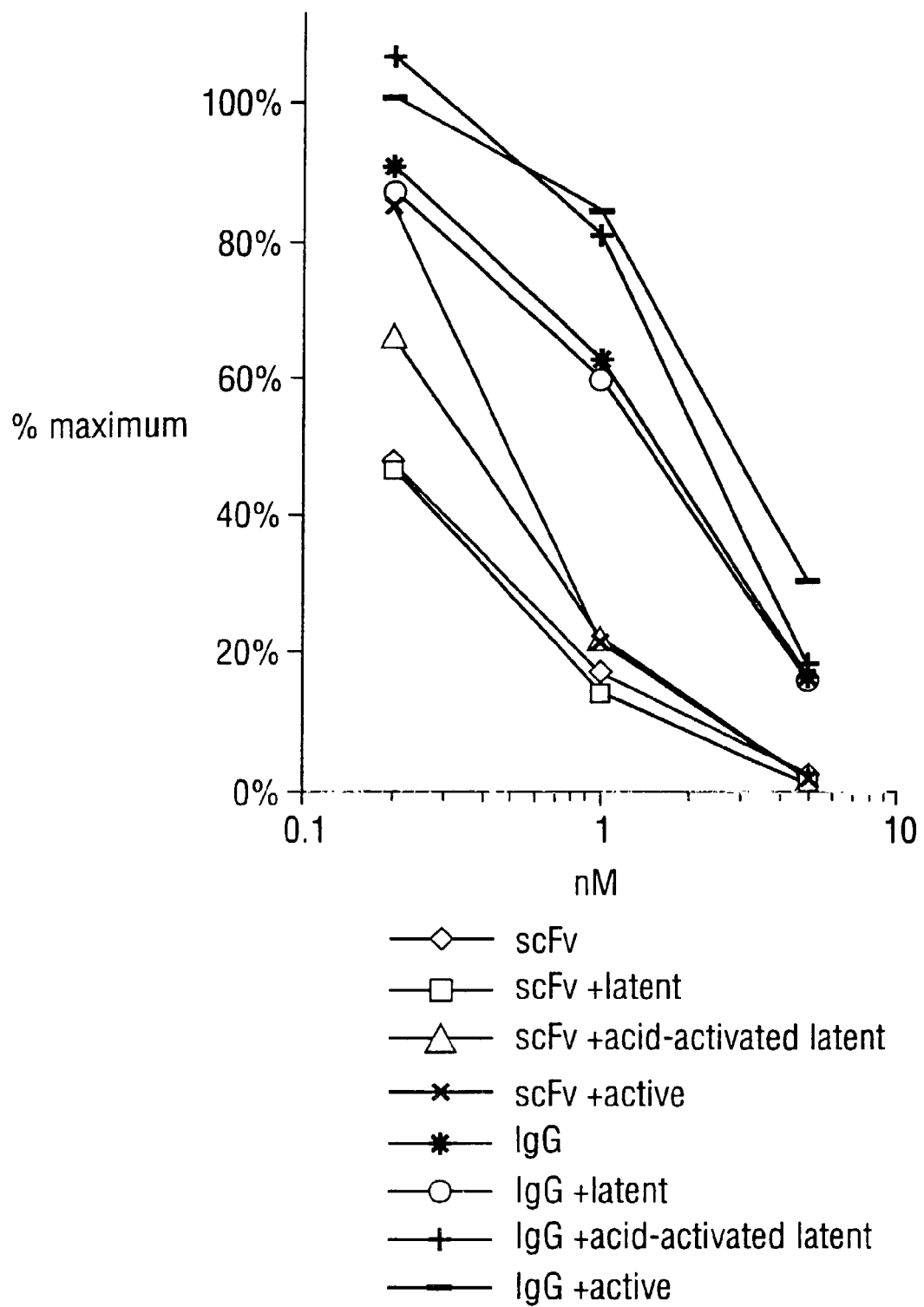

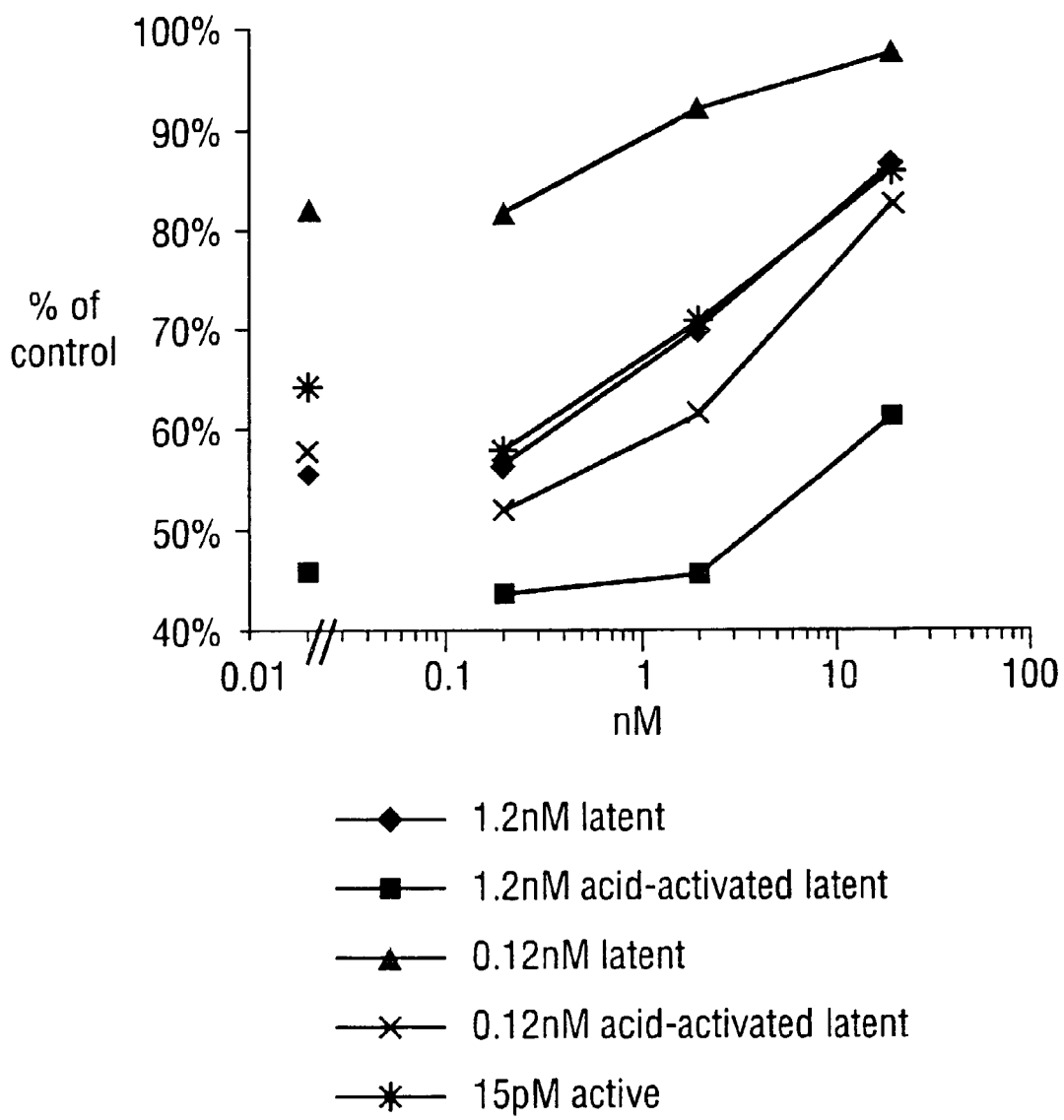

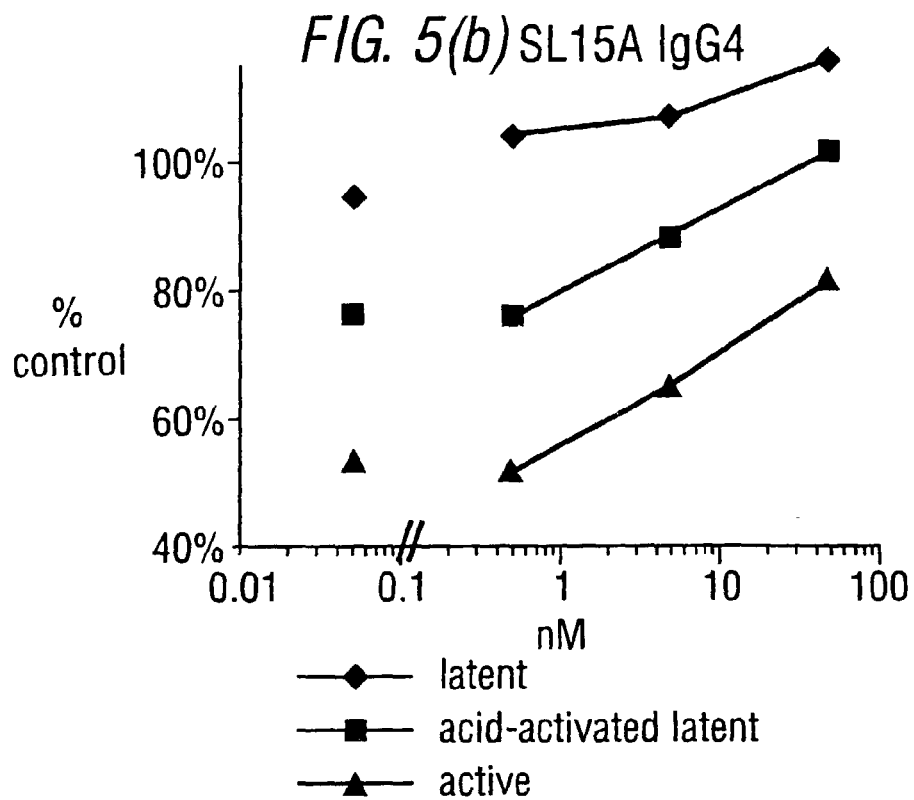
FIG. 5(b) SL15A IgG4
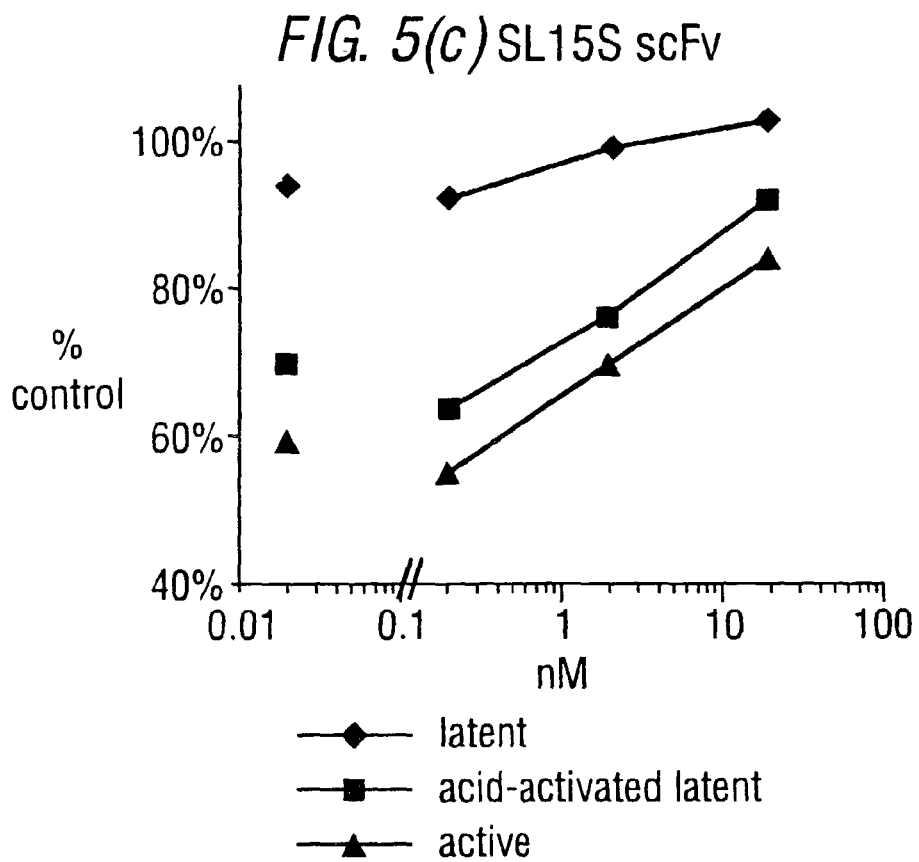
FIG. 5(c) SL15S scFv

FIG. 6
Inhibition of binding of CS37 using chimeric TGFβs

FIG. 7
Inhibition of binding of Kylie using chimeric TGFβs

Samples (x-axis): TGFb1, TGFb2, 1-1-2, 2-2-1, 1-2-2, 92-98

Legend: ▨ 0.8nM   ☐ 50nM   ▦ 100nM

SPECIFIC BINDING MEMBERS FOR TGFβ₁

The present application is a divisional of U.S. application Ser. No. 09/560,198, filed Apr. 28, 2000 now U.S. Pat. No. 6,492,497, which in turn is based on U.S. Provisional Application No. 60/131,983 filed Apr. 30, 1999.

FIELD OF THE INVENTION

The present invention relates to specific binding members, particularly antibodies and fragments thereof, which bind to transforming growth factor 1 (TGFβ₁). More particularly, the invention is concerned with specific binding members which include the VH CDR3 of the antibody SL15 (the antibody formerly known as Kylie), especially the SL15 VH domain, which may be in combination with the SL15A or SL15S VL domains Furthermore, the invention relates to use of such specific binding members in pharmaceutical preparations, particularly for the treatment of fibrotic disease, the modulation of wound healing and the treatment of cancer.

BACKGROUND TO THE INVENTION

PCT/GB96/02450 published as WO97/13844 discloses the isolation of human antibodies specific for human TGFβ₁ and human antibodies specific for human TGFβ₂ It describes antibodies with the 31G9 VH domain and variants of the domain More specifically the application described the antibody CS37 that comprises the 31G9 VH domain together with the CS37 VL and variants of this domain, including antibodies which:
 (i) compete in ELISA with CS37 for binding to TGFβ₁,
 (ii) bind TGFβ₁ preferentially with respect to TGFβ₃, and
 (iii) neutralise TGFβ₁.

DISCLOSURE OF THE INVENTION

The present invention is based on identification of antibodies which are related to CS37, but which have unexpectedly advantageous properties with respect to binding and neutralisation of TGFβ₁. They do not bind to, or neutralise, TGFβ₂ or TGFβ₃

Antibodies of the present invention strongly neutralise active TGFβ₁. The epitope for these antibodies lies in the C-terminal region of TGFβ₁ (residues 83–112) and includes the loop consisting of residues 92–98 of TGFβ₁, also known as finger 2, a region which has been identified as interacting with the receptor for TGFβ. The antibodies bind preferentially to active TGFβ₁ with respect to latent TGFβ₁

Variants of SL15S that strongly neutralise TGFβ₁ are also disclosed herein. These vary mainly by amino acid substitutions in the CDR3 of VH or VL domains There are, however, other sites where substitutions may be made, e.g. at residue 25 in the light chain an alanine may be substituted, generating the IgG4 antibody, SL15A IgG4, CAT-192. Several substitutions may be made that are compatible with the retention of strong neutralising activity. The antibodies of this invention will be particularly useful for treatment of fibrotic diseases, e.g. lung fibrosis, modulation of the scarring response, e.g. in wound healing and corneal scarring, and in other contexts discussed further below such as the treatment of tumors.

Specific binding proteins such as antibodies which are based on the complementarity-determining regions (CDRs) of the advantageous antibody VH and VL domains identified herein, particularly the CDR3 regions, will be useful for the purposes discussed, and represent aspects of the present invention.

The most preferred embodiments of the present invention in its various aspects are based on the VH CDR3 of the SL15 VH domain identified herein, VH domains including the SL15 VH CDR3, especially the SL15 VH domain itself, and pairings of such VH domains with VL domains, especially the SL15A or SL15S VL domains, or other VL domain comprising the SL15 VL CDR3. The antibody antigen-binding domain SL15 (in whichever format, e.g. scFv or IgG4) consists of the SL15 VH and, in two variants, either the SL15A VL (CS37) or SL15S VL (CS37 with A25S). In either variant, SL15 is the antibody formerly known as Kylie SL15S scFv is also known as CAT 191; SL15A IgG4 is also known as CAT-192, and SL15S IgG4 is also known as CAT-193

Further embodiments of the invention in its various aspects are based on the JT182 VH CDR3, VH domains including the JT182 VH CDR3, especially the JT182 VH domain, and pairings of such VH domains with VL domains, especially the CS37 VL domain. JT182 is not as effective as SL15, but still has unexpectedly improved properties over CS37.

In a first aspect the present invention provides an isolated specific binding member capable of binding TGFβ₁, wherein said specific binding member comprises an antigen binding domain comprising a VH CDR3 with an amino acid sequence substantially as set out as VH CDR3 of SL15 or JT182 in Table 1 or Table 2.

TABLE 1

Anti-TGFb1 Clones - CDR3s & Relative Potencies of scFv

| CLONE | Approx IC₅₀ (RRA) | VH CDR3 | VL CDR3 |
|---|---|---|---|
| CS37 | 10–15 nM | TGEYSGYDT<u>SGVEL</u> (SEQ ID NO: 14) | LQDSNYPLT (SEQ ID NO: 18) |
| JT182 | 0.5–1 nM | TGEYSGYDT<u>PASPD</u> (SEQ ID NO: 15) | CS37 |
| SL15 | 0.1 nM | TGEYSGYDT<u>DPQYS</u> (SEQ ID NO: 13) | CS37(+L25 A to S) |

Residues that differ between the scFv fragments are underlined.

The invention further provides said isolated specific binding member which further comprises a VH CDR1 or VH CDR2 with amino acid sequences substantially as set out as one or both of the VH CDR1 and VH CDR2 of the CS37 VH, preferably both (Table 2).

TABLE 2

CDR Sequences of CDRs of CS37, SL15 and JT182.

| Domain | CDR1 | CDR2 | CDR3 |
|---|---|---|---|
| CS37 VH | SYGMH (SEQ ID NO: 11) | VISYDGSIKYYADSVKG (SEQ ID NO: 12) | TGEYSGYDTSGVEL (SEQ ID NO: 14) |
| SL15 VH | SYGMH (SEQ ID NO: 11) | VISYDGSIKYYADSVKG (SEQ ID NO: 12) | TGEYSGYDTDPQYS (SEQ ID NO: 13) |

TABLE 2-continued

CDR Sequences of CDRs of CS37, SL15 and JT182.

| Domain | CDR1 | CDR2 | CDR3 |
|---|---|---|---|
| JT182 VH | SYGMH (SEQ ID NO: 11) | VISYDGSIKYYADSVKG (SEQ ID NO: 12) | TGEYSGYDTPASPD (SEQ ID NO: 15) |
| CS37 VL | RASQGIGDDLG (SEQ ID NO: 16) | GTSTLQS (SEQ ID NO: 17) | LQDSNYPLT (SEQ ID NO: 18) |
| SL15S VL | RSSQGIGDDLG (SEQ ID NO: 19) | GTSTLQS (SEQ ID NO: 17) | LQDSNYPLT (SEQ ID NO: 18) |

In a preferred embodiment, the binding domains are carried by a human antibody framework. One preferred example of such an embodiment is a VH domain with an amino acid sequence substantially as set out as the JT182 VH domain of which the sequence is set out in SEQ ID NO:10 A further preferred embodiment is a VH domain with an amino acid sequence substantially as set out as the SL15 VH domain, of which the sequence is set out in SEQ ID NO:4

In a second aspect, the invention provides an isolated specific binding member capable of binding $TGF\beta_1$, wherein said specific binding member comprises an antigen binding domain comprising a VL domain with an amino acid sequence substantially as set out as the SL15S VL domain, of which the sequence is set out in SEQ ID NO:8.

In a further aspect, the invention provides a specific binding member capable of binding $TGF\beta_1$, comprising a VH domain as set out above with respect to the first aspect, and a VL domain, preferably wherein the VL domain has an amino acid sequence substantially as set out as the CS37 VL (SL15A), of which the sequence is set out in SEQ ID NO:6, or the SL15S VL, of which the sequence is set out in SEQ ID NO:8.

In a particularly preferred embodiment, the invention provides a specific binding member comprising the CS37 VL domain and a VH domain selected from JT182 VH and SL15 VH, most preferably SL15 VH In a further particularly preferred embodiment, the invention provides a specific binding member comprising SL15 VH and SL15A VL (CS37 VL) or SL15S VL.

Preferred embodiments of the present invention provide specific binding members comprising the JT182 VH or SL15 VH domain in which 1, 2, 3, 4 or 5 amino acid substitutions have been made in a CDR, e g CDR3, and/or FR, which specific binding members retain ability to bind $TGF\beta_1$. Further preferred embodiments provide specific binding members comprising the SL15A (CS37) VL or SL15S VL, or SL15A or SL15S VL domain in which 1, 2, 3, 4 or 5 amino acid substitutions have been made in a CDR, e.g CDR3, and/or FR which specific binding members retain ability to bind $TGF\beta_1$. Such amino acid substitutions are generally "conservative", for instance substitution of one hydrophobic residue such as isoleucine, valine, leucine or methionine for another, or the substitution of one polar residue for another, such as arginine for lysine, glutamic for aspartic acid, or glutamine for asparagine. At certain positions non-conservative substitutions are allowable.

Such specific binding members are able to bind $TGF\beta_1$. Preferred embodiments lack significant cross-reactivity with $TGF\beta_2$ and/or $TGF\beta_3$, preferably $TGF\beta_2$ and $TGF\beta_3$ Preferred embodiments strongly neutralise $TGF\beta_1$, having a potency of at least 5 times better than does CS37, more preferably about 10 times, 15 times, 20 times, 50 times, 75 times, 100 times or 150 times better, in a radioreceptor assay (Lucas C et al (1991) *Meth in Enzymology* 198, 303–16) Potency is measured with the antibody under study and CS37 in equivalent molecular formats, e g as monovalent antibodies (scFv or Fab) or as bivalent antibodies (IgG1 or IgG4).

Preferred embodiments bind active $TGF\beta_1$ preferentially to latent $TGF\beta_1$.

Variants of the VH and VL domains and CDRs of which the sequences are set out herein and which can be employed in specific binding members for $TGF\beta_1$ can be obtained by means of methods of sequence alteration or mutation and screening. Such methods are also provided by the present invention.

In addition to antibody sequences, the specific binding member may comprise other amino acids, e.g forming a peptide or polypeptide, such as a folded domain, or to impart to the molecule another functional characteristic in addition to ability to bind antigen. Specific binding members of the invention may carry a detectable label, or may be conjugated to a toxin or enzyme (e.g. via a peptidyl bond or linker).

In further aspects, the invention provides an isolated nucleic acid which comprises a sequence encoding a specific binding member as defined above, and methods of preparing specific binding members of the invention which comprise expressing said nucleic acids under conditions to bring about expression of said binding member, and recovering the binding member.

Specific binding members according to the invention may be used in a method of treatment or diagnosis of the human or animal body, such as a method of treatment (which may include prophylactic treatment) of a disease or disorder in a human patient which comprises administering to said patient an effective amount of a specific binding member of the invention Conditions treatable in accordance with the present invention are described below.

These and other aspects of the invention are described in further detail below

All documents mentioned herein are incorporated by reference Sequences described herein are shown and referred to in the conventional 5' to 3' and N to C terminal notation for nucleic acid and amino acids sequences respectively, unless specifically indicated otherwise.

BRIEF DESCRIPTION OF THE FIGURES

FIG. 4: Inhibition of [$^{125}$I]TGFβ$_1$ binding to A549 cells by scFv in the presence of latent TGFβ$_1$. SL15S scFv and SL15A IgG4 were tested for their ability to inhibit [$^{125}$I]TGFβ$_1$ binding to A549 cells To investigate whether SL15S recognised latent TGFβ$_1$, the standard experiment was performed in the presence of 0.1 nM latent TGFβ$_1$, active TGFβ$_1$ or acid-activated latent TGFβ$_1$. Data are expressed as % max for each set of conditions.

FIG. 5: Neutralisation of TGFβ$_1$-induced inhibition of TF1 cell proliferation by scFv and IgG in the presence of latent TGFβ$_1$. The ability of SL15S scFv and SL15A IgG4 to neutralise the growth inhibition induced by latent TGFβ$_1$, active TGFβ$_1$ or acid-activated TGFβ$_1$ was compared in the TF1 assay In (a) varying concentrations of TGFβ$_1$ formats were compared where as in (b) scFv and IgG were compared against 20 pM TGFβ$_1$ formats. Data expressed as % control (growth in the absence of TGFβ$_1$). The inhibition induced by latent TGFβ$_1$ is due to the small amount of active TGFβ$_1$ present in the latent preparation.

FIG. 6: Inhibition of binding of CS37 scFv displayed on phage to TGFβ$_1$ using chimaeric TGFβs Binding of CS37 scFv displayed on phage to TGFβ$_1$ was assayed by ELISA in the presence of: the TGFβ$_1$ isoform (TGFβ$_1$); the TGFβ$_2$ isoform (TGFβ$_2$); TGFβ$_1$/β$_2$ (83–112) (1-1-2); TGFβ$_2$/β1 83–112 (2-2-1), TGFβ$_1$–β$_2$ (40–112) (1-2-2); or TGFβ$_1$–β$_2$ (92–98) (92–98)

FIG. 7. Inhibition of binding of SL15S (Kylie scFv) displayed on phage to TGFβ$_1$ using chimaeric TGFβs Binding of SL15S (Kylie) scFv displayed on phage to TGFβ$_1$ was assayed by ELISA in the presence of: the TGFβ$_1$ isoform (TGFβ$_1$); the TGFβ$_2$ isoform (TGFβ$_2$), TGFβ$_1$/β$_2$ (83–112) (1-1-2); TGFβ$_2$/β1 83–112 (2-2-1); TGFβ$_1$–β$_2$ (40–112) (1-2-2); or TGFβ$_1$–β$_2$ (92–98) (92–98).

DETAILED DESCRIPTION OF THE INVENTION

Terminology

Specific Binding Member

Figure 1A:
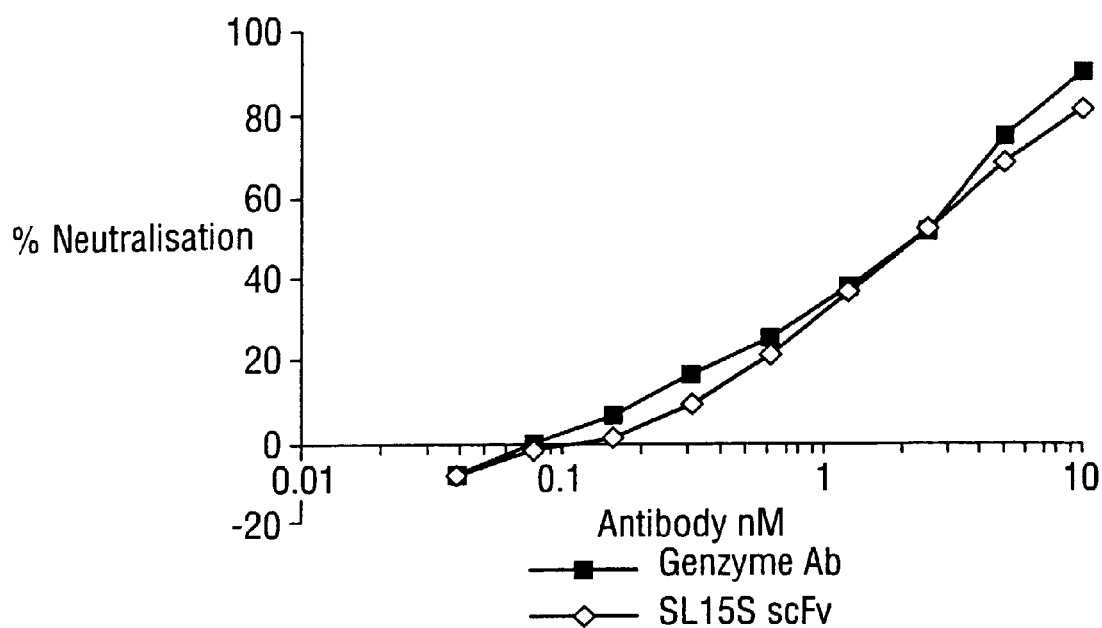
FIG. 1: Neutralisation of $TGF\beta_1$ but not $TGF\beta_2$ or β3 by SL15S scFv in a proliferation assay using TF1 cells. The neutralisation by Genzyme mAb (Mab 1D. 11.16-squares) or SL15S scFv (diamonds) of $TGF\beta_1$, $\beta_2$ or $\beta_3$-induced inhibition of proliferation of TF1 is shown.
Figure 1B:
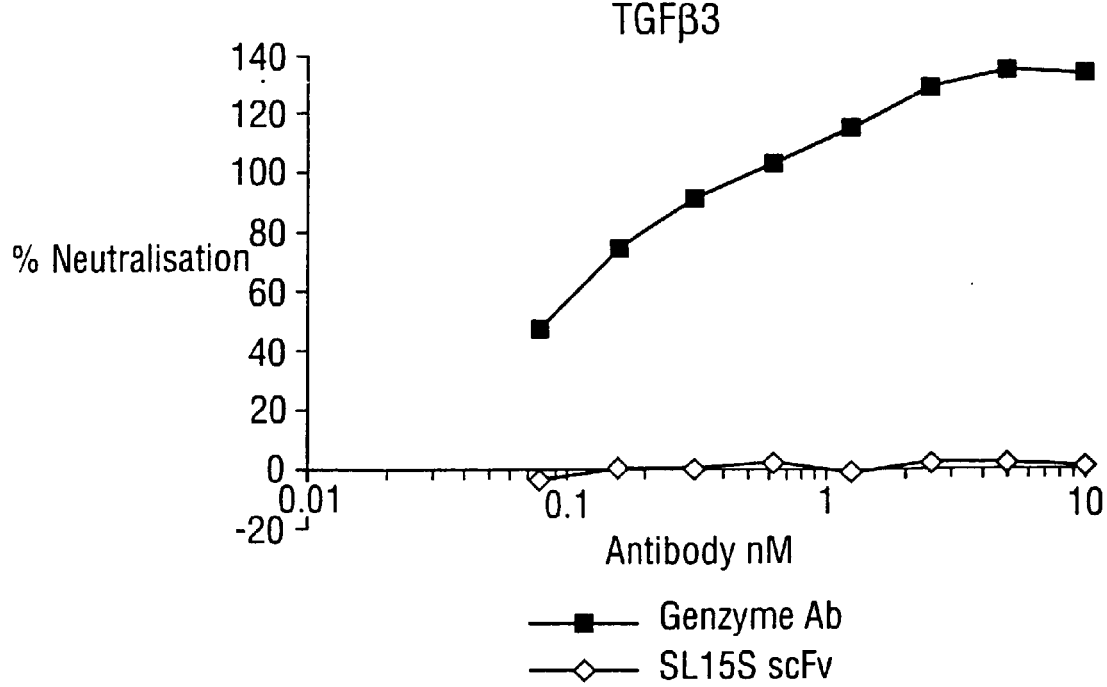
Figure 1C:
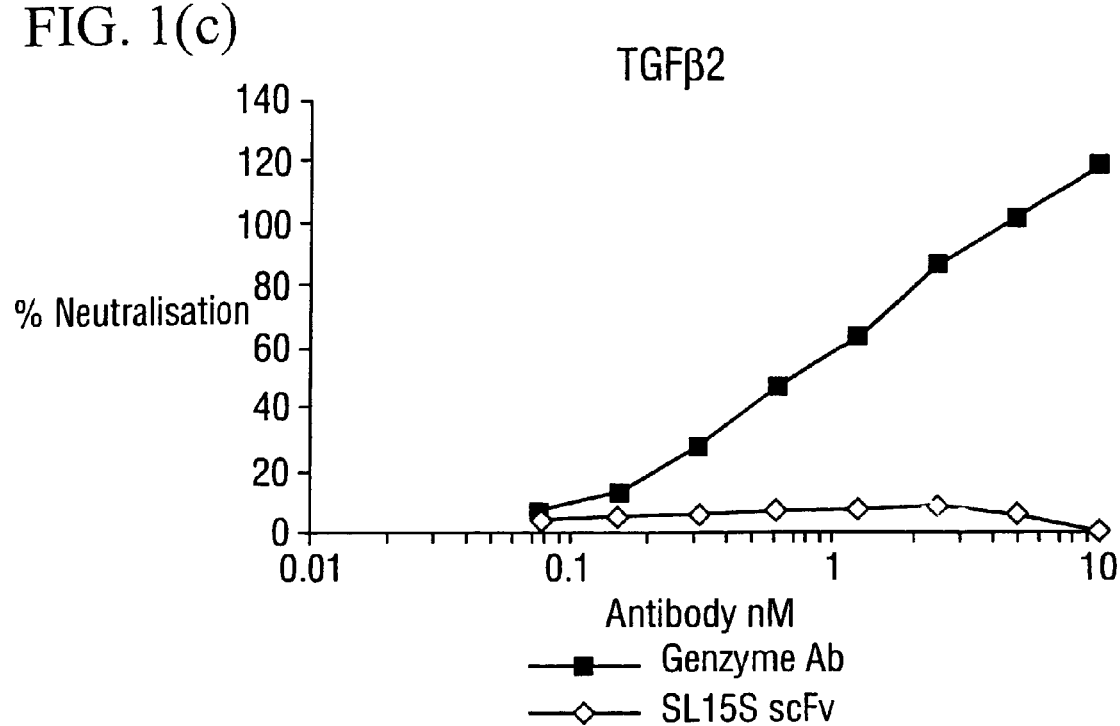
Figure 1D:
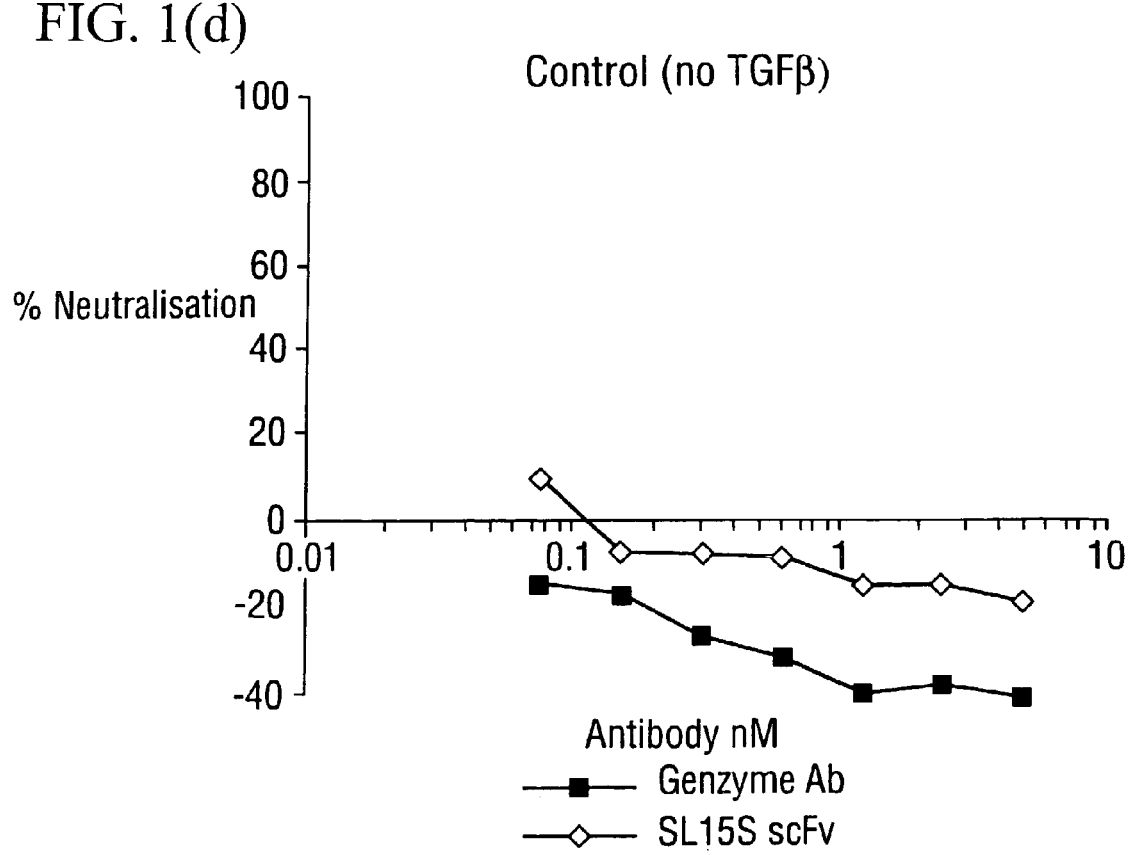

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

Antibody

This describes an immunoglobulin whether natural or partly or wholly synthetically produced. The term also covers any polypeptide or protein having a binding domain which is, or is substantially homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin See, for instance, EP-A-184187, GB 2188638A or EP-A-239400 A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341: 544–546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423–426, 1988; Huston et al, PNAS USA, 85, 5879–5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad Sci USA 90 6444–6448, 1993). Fv, scFv or diabody molecules may be stabilised by the incorporation of disulphide bridges linking the VH and VL domains (Y. Reiter et al, Nature Biotech, 14, 1239–1245, 1996). Minibodies comprising a scFv joined to a CH3 domain may also be made (S. Hu et al, Cancer Res., 56, 3055–3061, 1996).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804)

Where bispecific antibodies are to be used, these may be conventional bispecific antibodies, which can be manufactured in a variety of ways (Holliger, P. and Winter G. Current Opinion Biotechnol. 4, 446–449 (1993)), e.g prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al, Protein Eng., 9, 616–621, 1996).

Diabodies may be made with one binding site for $TGF\beta_1$ formed by VH and VL domains as disclosed in this application and the other binding site being for $TGF\beta_2$ The $TGF\beta_2$ binding site may be formed for instance from the VH and VL domains of the antibody 6B1 (WO97/13844).

Antigen Binding Domain

This describes the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). Preferably, an antigen binding domain comprises an antibody light chain variable region (VL) and an antibody heavy chain variable region (VH).

Specific

This may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

Comprise

This is generally used in the sense of include, that is to say permitting the presence of one or more features or components.

Isolated

This refers to the state in which specific binding members of the invention, or nucleic acid encoding such binding members, will be in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells (e.g. CHO or NSO (ECACC 85110503) cells, or they may be (for example if produced by expression in a prokaryotic cell) unglycosylated By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, substitutions may be made in the CDR and/or VH or VL domain The structure for carrying a CDR of the invention will generally be of an antibody heavy or light chain sequence or substantial portion thereof in which the CDR is located at a location corresponding to the CDR of naturally occurring VH and VL antibody variable domains encoded by rearranged immunoglobulin genes The structures and locations of immunoglobulin variable domains may be determined by reference to (Kabat, E. A. et al, Sequences of Proteins of Immunological Interest. 4th Edition. US Department of Health and Human Services. 1987, and updates thereof, now available on the Internet (http://immuno.bme.nwu.edu)). CDRs are generally as defined by Kabat. Additionally, in CDR grafting residues of the loop defined by Chothia adjacent the Kabat VH CDR1 may be grafted. For SL15S this would comprise residues 26 to 30 of the heavy chain (GFTGS).

Preferably, an amino acid sequence substantially as set out in Table 1 is carried as the CDR3 in a human heavy chain variable domain or a substantial portion thereof.

Variable domains employed in the invention may be derived from any germline or rearranged human variable domain, or may be a synthetic variable domain based on consensus sequences of known human variable domains. CDR-derived sequences of the invention may be introduced into a repertoire of variable domains lacking CDR3 regions, using recombinant DNA technology For example, Marks et al (*Bio/Technology*, 1992, 10: 779–783) describe methods of producting repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer (*Nature*, 1994, 370: 389–391), who describes the technique in relation to a β-lactamase gene but observes that the approach may be used for the generation of antibodies.

A further alternative is to generate novel VH or VL regions carrying a CDR-derived sequences of the invention using random mutagenesis of, for example, the SL15 or JT182 VH gene or SL15A or SL15S VL genes to generate mutations within the entire variable domain. Such a technique is described by Gram et al (1992, *Proc. Natl. Acad. Sci., USA*, 89: 3576–3580), who used error-prone PCR Another method which may be used is to direct mutagenesis to CDR regions of VH or VL genes. Such techniques are disclosed by Barbas et al, (1994, *Proc. Natl. Acad. Sci., USA*, 91: 3809–3813) and Schier et al (1996, *J. Mol. Biol.* 263: 551–567).

All the above described techniques are known as such in the art and in themselves do not form part of the present invention. The skilled person will be able to use such techniques to provide specific binding members of the invention using routine methodology in the art.

A further aspect of the invention provides a method for obtaining an antibody antigen binding domain specific for $TGF\beta_1$ and preferably one or more of the additional properties disclosed herein for specific binding members according to embodiments of the invention, the method comprising providing by way of addition, deletion, substitution or insertion of one or more amino acids in the amino acid sequence of a VH domain set out herein (SL15 or JT182) a VH domain which is an amino acid sequence variant of the VH domain, combining the VH domain thus provided with one or more VL domains, and testing the VH/VL combination or combinations to identify an antibody antigen binding domain specific for $TGF\beta_1$ and optionally with one or more of said preferred properties. Said VL domain may have an amino acid sequence which is substantially as set out for SL15A VL (CS37) or may have an amino acid sequence which is substantially as set out for VL.

An analogous method may be employed in which one or more sequence variants of a VL domain disclosed herein are combined with one or more VH domains.

A further aspect of the invention provides a method of preparing a specific binding member specific for $TGF\beta_1$, which method comprises a) providing a starting repertoire of nucleic acids encoding a VH domain which either include a CDR3 to be replaced or lack a CDR3 encoding region;

b) combining said repertoire with a donor nucleic acid encoding an amino acid sequence substantially as set out herein for SL15 or JT182 VH CDR3 such that said donor nucleic acid is inserted into the CDR3 region in the repertoire, so as to provide a product repertoire of nucleic acids encoding a VH domain, c) expressing the nucleic acids of said product repertoire; and d) selecting a specific binding member specific for $TGF\beta_1$; and e) recovering said specific binding member or nucleic acid encoding it.

Again, an analogous method may be employed in which a VL CDR3 of the invention is combined with a repertoire of nucleic acids encoding a VL domain which either include a CDR3 to be replaced or lack a CDR3 encoding region.

Similarly, one or more, or all three CDRs may be grafted into a repertoire of VH or VL domains which are then screened for a specific binding member or specific binding members specific for $TGF\beta_1$.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more details below.

Although in a preferred aspect of the invention specific binding members comprising a pair of VH and VL domains are preferred, single binding domains based on either VH or VL domain sequences form further aspects of the invention It is known that single immunoglobulin domains, especially VH domains, are capable of binding target antigens in a specific manner.

In the case of either of the single chain specific binding domains, these domains may be used to screen for complementary domains capable of forming a two-domain specific binding member able to bind $TGF\beta_1$.

This may be achieved by phage display screening methods using the so-called hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid.

Specific binding members of the present invention may further comprise antibody constant regions or parts thereof. For example, a VL domain such as SL15A VL or SL15S VL may be attached at their C-terminal end to antibody light chain constant domains including human Cκ or Cλ chains, preferably Cλ chains Similarly, specific binding members based on SL15 VH may be attached at their C-terminal end to all or part of an immunoglobulin heavy chain derived from any antibody isotype, e.g. IgG, IgA, IgE and IgM and any of the isotype sub-classes, particularly IgG1 and IgG4. IgG4 is preferred.

Antibodies of the invention may be labelled with a detectable or functional label. Detectable labels include radiolabels such as $^{131}$I or $^{99}$Tc, which may be attached to antibodies of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin.

Antibodies of the present invention are designed to be used in methods of diagnosis or treatment in human or animal subjects, preferably human.

Antibodies specific for human TGFβ$_1$ have been shown to be effective in animal models for the treatment of fibrotic diseases and other diseases where TGFβ$_1$ is overexpressed such as rheumatoid arthritis or cancer. Antibodies against TGFβ$_1$ have been shown to be effective in the treatment of glomerulonephritis (W. A. Border et al., *Nature*, 346: 371–374, 1990); neural scarring (A. Logan et al., *Eur. J. Neurosci.* 6: 355–363, 1994); dermal scarring (M. Shah et al., *Lancet* 339: 213–214, 1992, M. Shah et al., *J. Cell. Science* 107: 1137–1157,1994; M. Shah et al., 108 985–1002, 1995), and pulmonary fibrosis (Giri et al., *Thorax* 48: 959–966, 1993) Further, antibodies cross-reactive with the isoforms, TGFβs 1, 2 and 3, have been shown to be effective in models of lung fibrosis, radiation induced fibrosis (Barcellos-Hoff, U.S. Pat. No. 5,616,561 (1997)), myelofibrosis, burns, Dupuyen's contracture, gastric ulcers and rheumatoid arthritis (Wahl et al., *J. Exp. Medicine* 177: 225–230, 1993).

There are a number of further conditions associated with extracellular matrix deposition that may be ameliorated by administration of an antibody directed to TGFβ$_1$ These include systemic sclerosis, postoperative adhesions, keloid and hypertrophic scarring, proliferative vitreoretinopathy, glaucoma drainage surgery, corneal injury, cataract, Peyronie's disease, diabetic nephropathy, adult respiratory distress syndrome, cirrhosis of the liver, post myocardial infarction, post angioplasty restenosis, keloid scars, scarring after subarachnoid haemorrhage, multiple sclerosis, fibrosis after laminectomy, fibrosis after tendon and other repairs, tatoo removal, sclerosing cholangitis, pericarditis, pleurisy, tracheostomy, penetrating CNS injury, eosinophilic myalgic syndrome, vascular restenosis, veno-occlusive disease, pancreatitis and psoriatic arthropathy. In some cases treatment in combination with an antibody directed against TGFβ$_2$, such as 6B1 IgG4 (CAT-152) (see WO97/13844) may be valuably employed, for instance in the treatment of dermal scarring. The efficacy of SL15A IgG4 in treatment of corneal epithelial wound healing is demonstrated in Example 6.

The success of CAT-192 in promoting corneal wound healing provides indication of its usefulness in other conditions where promotion of re-epithelialisation is beneficial. These include diseases of the skin, such as venous ulcers, ischaemic ulcers (pressure sores), diabetic ulcers, graft sites, graft donor sites, abrasions and burns, diseases of the bronchial epithelium, such as asthma, ARDS, diseases of the intestinal epithelium, such as mucositis associated with cytotoxic treatment, oesophagual ulcers (reflex disease), stomach ulcers, small intestinal and large intestinal lesions (inflammatory bowel disease).

TGFβ also inhibits endothelial proliferation so anti-TGFβ antibodies may be used to stabilise atherosclerotic plaques and speed healing of vascular anastomoses. TGFβ may stimulate smooth muscle proliferation so anti-TGFβ treatment may be additionally appropriate or arterial disease and for asthma.

Asthma is a chronic inflammatory disorder of the airways manifesting as intermittent airflow obstruction, which over time may become progressive. Both in the allergic and non-allergic forms of the disease, there is evidence of an altered local T cell response in favour of the Th-2 cytokine release resulting on B-cell isotype switching to IgE, mast cell, eosinophil and basophil recruitment and activation and release of a wide range of inflammatory mediators. However, it has become clear that by itself, inflammation is not able to explain many of the features characteristic of chronic asthma and that restructuring of airway wall is also required (Holgate S T et al., *J. Allergy Clin. Immunol.* 2000 (in press)). This "remodelling" response accounts for the incomplete therapeutic efficacy of corticosteroids, with persistent bronchial hyperresponsiveness (BHR) (Lundgren R et al., (1988) *Eur. Respir. J.* 1(10): 883–889), and the progressive decline in pulmonary function over time, which occurs in those asthmatics with more chronic and severe disease (Lange P et al., (1998) *N. Engl. J. Med.* 339(17): 1194–1200).

Subepithelial and submucosal fibrosis is implicated in asthma. When assessed by high resolution CT, patients with severe asthma have thicker airways when compared to normal subjects or those with mild disease (Awadh N et al., (1998) *Thorax* 53(4): 248–253). This involves thickening and increased density of the SBM collagen layer, increases in smooth muscle and microvascular networks (Carroll N et al., (1993) *Am. Rev. Respir. Dis.* 147(2): 405–410). On the basis of measurements made in human airways and in a guinea pig model of chronic antigen exposure, SBM thickening reflects that of the entire airway wall. SBM-collagen thickness has been shown to correlate with disease severity, chronicity and BHR.

SBM thickening is due to the deposition of interstitial collagens Types I, III and V and fibronectin in the lamina reticularis and originates from the myofibroblasts whose numbers and activity are increased in asthma (Brewster C E et al., (1990) *Am. J. Respir. Cell Mol. Biol.* 3(5): 507–511) and further enhanced by allergen exposure (Gizycki M J et al., (1997) *Am. J. Respir. Cell Mol. Biol.* 16(6): 664–673). Bronchial biopsy and lavage studies have provided a compelling case for the epithelium as a potential source of profibrogenic growth factors. In asthma, immunostaining for TGFβ and b-FGF show both epithelial localisation and extensive staining of matrix, indicative of important interactions between these growth factors and matrix proteoglycans through specific glycosaminoglycan (GAG) binding sites (Redington A E et al., (1998) *J. Pathol.* 186(4): 410–415). Both TGFβ$_1$ and b-FGF are found in increased concentrations in lavage fluid, with further increases occurring after allergen exposure (Redington A E et al., (1997) *Am. J. Respir. Crit. Care Med.* 156(2, Pt 1): 642–647). Tissue analysis of growth factors, cytokines and chemokines have shown that these are mainly present in complex, high molecular weight forms. Latency associated peptide has been identified as the TGFβ binding molecule and using a bronchial explant model, it has been shown that allergen exposure of asthmatic mucosal tissue results in activation of TGFβ that is dependant upon plasmin activity, while b-FGF is released in soluble form by heparin and heparinase from mast cells and eosinophils respectively (McConnell W et al., Eur. Respir. J. 152s. 1999, Ref Type: Abstract).

Asthma is also involved in epthelial injury and airways remodelling. A characteristic feature of the remodelled airways in asthma is extensive epithelial damage caused by inflammatory cell products (Laitinen L A et al., (1985) Am. Rev. Respir. Dis. 131(4): 599–606). Mucosal damage not only allows tissue damaging molecules to pass unimpeded into the airways wall, but also causes the epithelium to become "activated" with expression of a variety of proinflammatory chemokines, autacoid mediators and adhesion molecules which contribute to chronic inflammation (Holgate S T et al., J. Allergy Clin. Immunol. 2000 (in press)). Injured and repairing epithelial cells are also important regulators of airway remodelling through increased production of fibroproliferative and profibrogenic growth factors including TGFβ isoforms (Zhang S et al., (1999) Lab. Invest. 79(4): 395–405). It has recently been found that impairment of epidermal growth factor receptor (EGFR)-mediated epithelial repair causes greatly increased release of $TGFβ_2$ by damaged epithelial cells and a marked enhancement of collagen III gene expression when conditioned medium is added to myofibroblast cultures. As TGFβ isoforms are potent inhibitors of epithelial cell proliferation, excessive production of TGFβ in asthma may account for the unexpectedly low level of expression of the proliferation marker PCNA found in asthmatic epithelium (Demoly P et al., (1994) Am. J. Respir. Crit. Care Med. 150(1): 214–217). In this way, conditions that favour collagen biosynthesis by the sub-epithelial myofibroblasts, may also contribute to disease chronicity by retarding epithelial repair. Hence reducing TGFβ levels by the use of specific binding members of the present invention would be expected to address the need in chronic and severe asthma to prevent matrix protein biosynthesis by bronchial myofibroblasts, as well as promoting bronchial epithelial repair in order to restore a non-activated epithelial phenotype and normal barrier function.

$TGFβ_1$ also modulates immune and inflammatory responses, for instance in response to malignancy and infection. An antibody against $TGFβ_1$ may be used for improving the immune response to infections such as hepatitis B, hepatitis C or tuberculosis or for reducing immunosuppression induced, for instance, by tumors or AIDS infection or granulomatous diseases An antibody against $TGFβ_1$ may be useful for treatment of acute and chronic rejection of organ transplant and malignant tumors, and may be used in prevention of the spread of cancer cells induced by treatment with cyclosporine.

An antibody against $TGFβ_1$ may be used as an adjuvant for immunotherapy.

An antibody against $TGFβ_1$ may be used for inhibition of angiogenesis, for instance in treatment of tumors. The majority of tumor cells express detectable levels of $TGFβ_1$ (Wojtowicz-Praga 1997, J. Immunother. 20 (3): 165–77). Furthermore, cells that produce higher levels of $TGFβ_1$ have a higher metastatic (Blanckaert et al., 1993, Cancer. Res. 53 (17): 4075–81) or invasive (Arteaga et al., 1993, Cell Growth and Differentiation 4(3):193–201) potential. In many cancers $TGFβ_1$ plasma levels are correlated with disease progression. Thus the source of $TGFβ_1$ can be the tumor cells as well as surrounding tissue TGFβ is a potent suppressor of malignant transformation in normal healthy epithelial tissue and can inhibit proliferation However, many advanced cancers become resistant to the growth-inhibitory actions of TGFβ as a result of abnormalities in the type II TGFβ receptor (Markowitz et al, 1995, Science 268 (5215): 1336–8) or SMAD signal transduction (Hata et al., 1998, Mol. Med. Today 4(6): 257–62).

Tumours require a blood supply for growth in excess of 1 $mm^3$ and for metastasis (Folkman 1995, Breast Cancer Res. Treat. 36 (2): 109–18). This has led to the rapid development of anti-angiogenic treatments for solid tumors.

$TGFβ_1$ has been shown to cause angiogenesis indirectly by up regulating VEGF production in vitro and in vivo. Breast cancers contain large numbers of infiltrating macrophages. The role and function of these cells within the tumor remain unclear, but a number of studies have found an association with poor prognosis. Both tumor cells and tumor macrophages produce VEGF in vitro and production is up regulated by $TGFβ_1$. Serum VEGF level is enhanced in patients with breast cancer and these levels directly correlate to serum $TGFβ_1$ levels. Thus, $TGFβ_1$ expression by breast cancer cells and cancer-associated macrophages may elicit an angiogenic response through generation of VEGF (Donovan et al, 1997, Ann. Surg. Oncol. 4 (8): 621.7, Harmey et al., 1998, Ann. Surg. Oncol. 5(3): 271–278).

Ueki et al. (1992, Japanese Journal of Cancer Research 84(6): 589–93) demonstrated that $TGFβ_1$ enhanced tumor growth in vivo. This group transected CHO cells with the $TGFβ_1$ gene resulting in overexpression of $TGFβ_1$. $TGFβ_1$-secreting CHO cells were shown to grow more rapidly that non-transected cells when injected subcutaneously into nude mice. Prominent vascularisation was observed in tumors derived from $TGFβ_1$-transected cells; vascularisation was diminished in the non-transected cells. In addition, an anti-$TGFβ_1$ neutralising antibody was able to inhibit both growth and angiogenesis in the tumors derived from $TGFβ_1$-transected cells. Thus, overproduction of $TGFβ_1$ by tumor cells contributed to tumor growth and neovascularisation.

It is known that patients who have cancer also have a defective immune system. Recently $TGFβ_1$ has been suggested to play a key role in tumor-associated immunosuppression. This topic has been the focus of a recent review (Wojtowicz-Praga, 1997, ibid). Certainly, $TGFβ_1$ appears to be a potent immunosuppressor, and it has been consistently detected from a variety of tumor cell lines and in plasma of tumor-bearing hosts.

Neutralisation of $TGFβ_1$ by monoclonal antibodies or inhibition of production by antisense results in attenuation of tumor growth and metastatic ability in animal models. Growth of MCF-7 breast cancer cells transected with $TGFβ_1$ in mice is prevented with 2G7 (repeated i.p. does), an anti-$TGFβ_{1,2,3}$ antibody (Arteaga et al., ibid). Growth of normal MCF-7 cells is prevented by 2G7 but only when treatment started at the time of tumor cell inoculation. Further, more convincing evidence for an action of anti-TGFβ antibodies to relive tumor-induced immunosuppression has been provided (Arteaga et al., J. Clin. Invest. 92 (6): 2569–2576). MDA-231, a human breast cancer cells line caused a decrease in spleen natural killer (NK) cell activity in nude mice following i.p. inoculation. 2G7 (200 μg every 2 days, i.p.) attenuated intra-abdominal tumors and lung metastasis as well as markedly increasing the activity of spleen NK cell activity. Furthermore, conditioned medium from cultures of MDA-231 tumor cells inhibited the NK cell activity of human blood; again 2G7 prevented this. Growth of subcutaneous xenografts of MDA-231 cells were only transient inhibited by 2G7. The action of 2G7 on tumor growth, metastasis, and NK cell activity were absent in beige NK cell-deficient nude mice (Arteaga et al., *J. Clin. Invest.* 92 (6): 2569–2576).

In a further study, the 2G7 anti-TGFβ antibody (500 μg i.p. every other day) in combination with IL-2 (10000U i.p. 2× daily) was able to reduce B16 melanoma lung metastasis but was not as effective i.v. inoculation. 2G7 alone also reduced the number of lung metastasis but was not as effective as the combined therapy Plasma $TGF\beta_1$ levels were significantly reduced in the antibody treated animals (Wojtowicz-Praga et al., 1996, *J. Immunother. Emphasis Tumor Immunol.* 19(3): 169–175). Two previous studies either failed to show an effect or only caused a small effect using the combination of anti-$TGF\beta_1$ and IL-2 (Gridley et al., 1993, *Cancer Biother.* 8 (2): 159–170; Mao et al, 1994, *Cancer Biother.* 9(4): 317–327, respectively), however, the doses of anti-$TGF\beta_1$ antibodies used in these studies were small (100 ng and 1 μg respectively) Thus, combination of anti-TGFβ therapy with immunostimulation would appear, from animal model data, to provide proof of concept for this therapeutic approach to cancer Hoefer and Anderer (1995, *Cancer Immunol. Immunother.* 41 (5): 302–308) demonstrated that the human carcinoma cell line, SLU-1, and the highly metastatic sub-line SLU-M1, resulted in metastasis in nude mice following s c. inoculation. The incidence of metastasis as well as primary tumor growth was reduced by treatment with anti-$TGF\beta_1$ antibodies (treatment from day 3, every 3–4 days with 100 μg s.c. at the tumor site) The authors suggested that the antibodies reversed $TGF\beta_1$-induced immunosuppression leading to inhibition of tumor growth and metastasis.

Previous work has also demonstrated that anti-TGFβ antibodies can reduce tumor metastasis in vivo (Arteaga et al., 1993, *J. Clin., Invest.* 92(6): 2569–2576; Hoefer & Anderer, 1995, ibid; Wojtowicz-Praga et al., 1996, ibid). Initial conclusions from these studies suggested that $TGF\beta_1$-induced immunosuppression permitted metastasis of these tumor xenografts. However, a recent paper suggests that $TGF\beta_1$ may enhance the invasive and metastatic potential of cells directly (Hojo et al., 1999, *Nature* 397: 530–534). Cyclosporin dose-dependently induces $TGF\beta_1$ release from human pulmonary adenocarcinoma cells in culture, however, the mechanism of TGFβ production by cyclosporin is not known. Treatment of adenocarcinoma cells with cyclosporin (or $TGF\beta_1$) results in membrane ruffling, pseudopodia formation, anchorage-independent (invasive) growth and motility. An anti-$TGF\beta_1$ antibody inhibits these cell morphology and motility changes in vitro. Similar observations were made for renal cells adenocarcinoma, mammary gland epithelial cells and mink lung epithelial lung cells. In immunodeficient SCID-beige mice (deficient in T cells, B cells, NK cells), cyclosporin increased the number of metastasis following incubation (i v.) Of murine renal cell adenocarcinoma, Lewis lung carcinoma or human bladder cancer cells. Treatment with the anti-$TGF\beta_{1,2,3}$ neutralising antibody, 1D11.16 (200 μg per pay, initial dose 1 day prior to tumor cell inoculation) significantly reduced the number of pulmonary metastasis in cyclosporin treated mice (to levels below that of the non-cyclosporin treated control group). Thus, it appears and in that cyclosporin can, through an action dependant on $TGF\beta_1$ production, increase invasion and metastasis in animal models independent of the host's immune system (Hojo et al., 1999, ibid).

Evidence from in vitro and in vivo models suggests that $TGF\beta_1$, can enhance tumor formation utilising three main mechanisms; angiogenesis, immunosuppression and phenotypic changes of tumor cells to increase invasive and metastatic behaviour. Thus, inhibition of $TGF\beta_1$ would be expected to inhibit malignancy in man and within a single molecule, deliver a combined anti-cancer therapy.

Cancers in which $TGF\beta_1$ have been implicated include breast, prostate, ovarian, stomach, colerectal, skin, lung, cervical and bladder cancers, as well as various leukemias and sarcomas, such as Kaposi's Sarcoma. Accordingly, antibodies of the invention may be administered for the treatment of cancers in which $TGF\beta_1$ is implicated either angiogensis, metastasis or tumor progression, including cancers of the foregoing conditions. It will of course be appreciated that in the context of cancer therapy, "treatment" includes any medical intervention resulting in the slowing of tumor growth or reduction in tumor metastases, as well as partial remission of the cancer in order to prolong life expectancy of a patient.

Antibody therapy for the treatment of cancer is an established treatment in the art. Three anti-cancer antibodies are currently licenced for clinical use in the US and/or Europe (Panorex for the treatment of colorectal cancer, Rituxan for B-cell lymphoma and Herceptin for breast cancer), in addition to numerous other anti-cancer antibodies currently in Phase I, II or III clinical trials. These antibodies are often used in late stage treatment and are considered effective by the criteria of the preceding paragraph, as well as, in some cases, providing complete remission of the tumor.

Accordingly, further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated Prescription of treatment, eg decisions on dosage etc, is within the responsibility of general practitioners and other medical doctors. Appropriate doses of antibody are well known in the art; see Ledermann J. A. et al (1991) *Int J. Cancer* 47: 659–664; Bagshawe K. D. et al. (1991) *Antibody, Immunoconjugates and Radiopharmaceuticals* 4: 915–922.

A composition may be administered alone or in combination with other treatments, either simultaneously or sequentially dependent upon the condition to be treated.

Antibodies of the present invention may be administered to a patient in need of treatment via any suitable route, usually by injection into the bloodstream or directly into the site to be treated, e g. cornea, wound, tumor, etc. The precise dose will depend upon a number of factors, including whether the antibody is for diagnosis or for treatment, the size and location of the area to be treated (e.g. wound), the precise nature of the antibody (e.g. whole antibody, fragment or diabody), and the nature of any detectable label or other molecule attached to the antibody. A typical antibody dose will be in the range 0.5 mg to 100 g for systemic applications, such as treatment of fibrosis in glomerulonephritis or in the treatment of cancers and 10 μg to 1 mg for local applications such as treatment of dermal scarring. Typically, the antibody will be a whole antibody, preferably the IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

It is presently preferred that a whole antibody of the IgG4 isotype is used for systemic and local applications but for local applications a scFv antibody may be particularly valuable.

Specific binding members of the present invention will usually be administered in the form of a pharmaceutical composition, which may comprise at least one component in addition to the specific binding member Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil Physiological saline solution, dextrose or other saccharide solution or glycols such as ethylene glycol, propylene glycol or polyethylene glycol may be included. Formulation as eye drops may be valuable for prevention or treatment of ocular fibrosis or scarring.

For intravenous, injection, or injection at the site of affliction, the active ingredient will be in the form of a parenterally acceptable aqueous solution which is pyrogen-free and has suitable pH, isotonicity and stability Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The antibody may be administered from a sustained delivery system to prevent fibrosis or may be coated onto prosthetic devices, such as hip replacements, to prevent development of fibrosis associated with their insertion A composition may be administered alone or in combination with other treatments, either simultaneously or sequentially dependent upon the condition to be treated. Other treatments may include the administration of suitable doses of pain relief drugs such as non-steroidal anti-immflamatory drugs (e.g. asprin, paracetamol, ibuprofen or ketoprofen) or opitates such as morphine, or anti-emetics.

The present invention provides a method comprising causing or allowing binding of a specific binding member as as provided herein to $TGF\beta_1$. As noted, such binding may take place in vivo, e.g. following administration of a specific binding member, or nucleic acid encoding a specific binding member, or it may take place in vitro.

The amount of binding of specific binding member to $TGF\beta_1$ may be determined. Quantitation may be related to the amount of $TGF\beta_1$ in a test sample, which may be of diagnostic interest, which may be of diagnostic interest, for example, measurement of $TGF\beta_1$ has also been proposed as an indicator for atherosclerosis, low concentrations being correlated with advanced atherosclerosis.

The reactivities of antibodies on a sample may be determined by any appropriate means. Radioimmunoassay (RIA) is one possibility. Radioactive labelled $TGF\beta_1$ is mixed with unlabelled $TGF\beta_1$ (the test sample) and allowed to bind to the antibody. Bound $TGF\beta_1$ is physically separated from unbound $TGF\beta_1$ and the amount of radioactive $TGF\beta_1$ bound to the antibody determined. The more $TGF\beta_1$ there is in the test sample the less radioactive $TGF\beta_1$ will bind to the antibody. A competitive binding assay may also be used with non-radioactive $TGF\beta_1$, using $TGF\beta_1$ or an analogue of $TGF\beta_1$ linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are colored, magnetic or paramagnetic, and biologically or chemically active agents that can directly or indirectly cause detectable signals to be visually observed, electronically detected or otherwise recorded. These molecules may be enzymes which catalyse reactions that develop or change colors or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of a specific binding member as above for measuring $TGF\beta_1$ levels in a competition assay, that is to say a method of measuring the level of $TGF\beta_1$ in a sample by employing a specific binding member as provided by the present invention in a competition assay This may be where the physical separation of bound from unbound $TGF\beta_1$ is not required. Linking a reporter molecule to the specific binding member so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of $TGF\beta_1$ directly, by employing a specific binding member according to the invention for example in a biosensor system.

The mode of determining binding is not a feature of the present invention and those skilled in the art are able to choose a suitable mode according to their preference and general knowledge.

The present invention further extends to a specific binding member which competes for binding to $TGF\beta_1$ with any specific binding member which both binds $TGF\beta_1$ and comprises a V domain including a CDR with amino acid substantially as set out herein or a V domain with amino acid sequence substantially as set out herein. Competition between binding members may be assayed easily in vitro, for example by tagging a specific reporter molecule to one binding member which can be detected in the presence of other untagged binding member(s), to enable identification of specific binding members which bind the same epitope or an overlapping epitope. Competition may be determined for example using the TGFβ$_1$ ELISA as described in Example 1.

Preferred specific binding members for TGFβ$_1$ compete for binding to TGFβ$_1$ with CAT 191, CAT 192 and/or CAT 193

Preferred embodiments strongly neutralise TGFβ$_1$, having a potency of at least 5 times better than does CS37, more preferably about 10 times, 15 times, 20 times, 50 times, 75 times, 100 times or 150 times better, in a radioreceptor assay (Lucas C et al (1991) *Meth in Enzymology* 198: 303–316). Potency is measure with the antibody under study and CS37 in equivalent molecular formats, e.g as monovalent antibodies (scFv or Fab) or as bivalent antibodies (IgG1 or IgG4).

In one aspect, a specific binding member according to the present invention binds a peptide including the amino acid sequence of residues 92–98 of TGFβ$_1$ (the same epitope as CS37).

In testing for this, a peptide with this sequence plus one or more amino acids at either end, may be used. Such a peptide may be said to "consist essentially" of the specified sequence. Specific binding members according to the present invention may be such that their binding for TGFβ$_1$ is inhibited by a peptide with or including the sequence given. In testing for this, a peptide with either sequence plus one or more amino acids may be used Specific binding members which bind a specific peptide may be isolated for example from a phage display library by panning with the peptide(s).

The present invention further provides an isolated nucleic acid encoding a specific binding member of the present invention. Nucleic acid includes DNA and RNA. In a preferred aspect, the present invention provides a nucleic acid which codes for a CDR or VH or VL domain of the invention as defined above.

The present invention also provides constructs in the form of plasmids, vectors, transcription or expression cassettes which comprise least one polynucleotide as above.

The present invention also provides a recombinant host cell which comprises one or more constructs as above. A nucleic acid encoding any CDR, VH or VL domain, or specific binding member as provided itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression a VH or VL domain, or specific binding member may be isolated and/or purified using any suitable technique, then used as appropriate.

Specific binding members, VH and/or VL domains, and encoding nucleic acid molecules and vectors according to the present invention may be provided isolated and/or purified, e.g from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545–551 (1991). Expression in eukaryotic cells in culture is also available to those skilled in the art as an option for production of a specific binding member, see for recent reviews, for example Reff, M. E. (1993) *Curr. Opinion Biotech.* 4: 573–576, Trill J. J. et al. (1995) *Curr. Opinion Biotech* 6: 553–560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual: 2nd edition*, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above The following examples illustrate aspects and embodiments of the present invention.

Example 1 Identification of SL15 S scFv (CAT-191) and JT 182

Example 2 Construction of cell lines expressing the antibody SL15A IgG4 (CAT-192) and SL15S IgG4 (CAT-193)

Example 3 Assessment of neutralisation properties of SL15S scFv (CAT-191) and SL15A IgG4 (CAT-192) and SL15S IgG4 (CAT-193)

Example 4 Binding of the antibody SL15S scFv (CAT-191) and SL15A IgG4 (CAT-192) to active and latent TGFβ$_1$ Example 5 Epitope mapping of the antibodies SL15S scFv and CS37 scFv

EXAMPLE 1

Identification of SL15S scFv (CAT-191) and JT182

The present inventors have identified antibody CDRs and VH and VL domains related to those of the CS37 antibody disclosed in WO97/13844, but with unexpectedly good properties.

The CS37 VH (31G9) domain sequence and encoding nucleic acid therefor are shown in SEQ ID NO:2 and SEQ ID NO:1, respectively.

The SL15 (a.k.a. KYLIE) VH domain sequence of the present invention and encoding nucleic acid therefor are shown in SEQ ID NO:4 and SEQ ID NO:3, respectively The respective VH CDR3 sequences are shown in Table 1, also Table 2 which includes CDR1 and CDR2 sequences for both VH and VL domains.

Comparison of CS37 (31G9) and SL15 (Kylie) VH domains shows three further differences in framework residues, at residues 1 (glutamine CS37 to glutamate SL15), 6 (glutamine CS37 to glutamate SL15) and 44 (glycine CS37 to glutamate SL15).

The SL15 VH domain may be paired with different VL domains, and two such SL15 variants have been identified. One, known as SL15A, includes the CS37 VL. The other, known as SL15S, includes a VL which corresponds to the CS37 VL save for the presence of Serine at residue 25 in SL15S compared with alanine in SL15A (CS37).

The SL15A VL (CS37) domain sequence and encoding nucleic acid therefor are shown in SEQ ID NO:6 and SEQ ID NO:5, respectively.

The SL15S VL domain sequence and encoding nucleic acid therefor are shown in SEQ ID NO:8 and SEQ ID NO:7, respectively.

The JT182 VH domain sequence and encoding nucleic acid therefor are shown in SEQ ID NO:10 and SEQ ID NO:9, respectively.

SL15S scFv, CS37 scFv and a related antibody JT182 were screened as phage supernatants in ELISA assays for the ability to bind TGFβ$_1$. ELISA plates (96 well; Falcon) were uncoated, or coated with recombinant TGFβ$_1$ (0.2 μg/ml). Phage that bound specifically to the antigen coated plate were detected using a sheep anti-fd antiserum (Pharmacia), followed by alkaline phosphatase conjugated anti-sheep (Sigma) and p-nitrophenyl phosphate (pNPP) substrate (Sigma).

The scFv fragments were subsequently tested for their ability to neutralise binding of $^{125}$I-TGFβ$_1$ to A549 cells in a radioreceptor binding assay (RRA), using the protocol described in Example 3 (see below). For the RRA, individual clones were expressed as soluble scFv and subsequently purified from periplasmic preparations by immobilised metal affinity chromatography (IMAC) followed by fractionation of monomeric scFv by gel filtration FPLC on a Superdex 75 column (Pharmacia).

SL15 scFv (SL15 VH/SL15 VL) has the highest neutralisation potency in the RRA, having an IC$_{50}$ of 100 pM which is at least 100 fold better than CS37. The complete specificity of SL15 scFv for the TGFβ$_1$ isoform has been confirmed in the TF1 assay where no interaction with TGFβ$_2$ or TGFβ$_3$ was detected.

The scFv antibodies SL15S (SL15 VH/SL15 VL; CAT-191 a.k.a. Kylie scFv) and SL15A (SL15 VH/CS37VL) were converted into whole antibody.

EXAMPLE 2

Construction of Cell Lines Expressing the Antibody SL15A IGG4 (CAT-192) and SL15S IGG4 (CAT-193)

For the construction of cell lines expressing human IgG4, κ antibodies, SL15 scFV heavy and light chain variable domains were cloned into mammalian expression vectors containing human IgG4 and human kappa constant domains respectively. Two versions were prepared, SL15A IgG4 (CAT-192) and SL15S IgG4 (CAT-193) The antibodies are also termed Kylie IgG Heavy Chain Expression Vector The VH from the SL15S scFv DNA was PCR-amplified with oligonucleotides P80 (SEQ ID NO:25) and P64 (SEQ ID NO:22) and joined by overlapping PCR to a 159 bp DNA fragment containing a signal sequence, splice sites and intron from M13VHPCR1 (Orlandi et al., 1989, *Proc. Natl. Acad. Sci. USA* 86: 3833–3837) using oligonucleotides P10 (SEQ ID NO:20) and P64 (SEQ ID NO:22). The 558 bp PCR product was cut with HindIII and ApaI and cloned into HindIII-ApaI cut pGamma4 (obtained from Lonza Biologics). Ligated DNA was transformed into *E. coli* TG1 and ampicillin-resistant colonies screened. A plasmid with the correct insertion was identified and designated pKylieVHγ4.

Light Chain Expression Vector

The Vκ from the CS37 scFv DNA or from SL15S scFv was PCR-amplified with oligonucleotides P65 (SEQ ID NO:23) and P66 (SEQ ID NO:24) and joined by overlapping PCR to a 168 bp DNA fragment containing a signal sequence, splice sites and intron from M13VKPCR1 (Orlandi et al., 1989, *Proc. Natl. Acad. Sci. USA* 86; 3833–3837) using oligonucleotides P11 (SEQ ID NO:21) and P66 (SEQ ID NO:24). The 510 bp PCR product was cut with BstBI and BsiWI and cloned into BstBI-BsiWI cut pMR15.1 Ligated DNA was transformed into *E. coli* TG1 and ampicillin-resistant colonies screened. A plasmid with the correct insertion was identified and designated pCS37κ or pKylieκ.

Tandem Expression Vector

A single plasmid containing both heavy and light chain DNAs and the gs selectable marker was constructed for each of the Kylie variants The heavy chain vector, pKylieVHγ4, was digested with BamHI and NotI and the 4497 bp fragment containing H chain DNA purified. The light chain vector, pCS37Vκ or pKylieκ, was similarly cut with BamHI and NotI and the 9611 bp fragment containing L chain DNA was isolated. The two purified fragments were ligated together, transformed into *E. coli* TG1 cells and ampicillin-resistant colonies screened. A plasmid with the correct insertions was identified and the V regions confirmed by sequencing. The final expression vector was designated pKylieg4γs. Two versions were prepared containing SL15S VL or CS37 VL.

Expression of SL15S IgG4 and SL15A IgG4

SL15S IgG4 and SL15A IgG4 were expressed in the mouse myeloma cell line NS0 (ECACC 85110503) Fifty μg of pKylieg4γs were linearised by digestion with PvuI, ethanol precipitated and dissolved in 100 μl water. 10$^7$ NS0 cells were washed in PBS, resuspended in 0.9 ml PBS, mixed with the vector DNA and held in ice for 5 min. The cells were then electroporated with a single pulse of 250 V at 960 μFd and incubated in ice for 10 min. The transfected cells were then added to 30 ml Dulbecco's modified Eagle's medium (DMEM) containing 2 mM glutamine and 10% dialysed foetal calf serum (FCS) as described by Bebbington et al. (1992) *Bio/Technology*, 10: 169–175, and 50 µl aliquots distributed into 6×96-well plates. 24 h later glutamine-free DMEM/10% FCS (Bebbington et al. 1992) was added to each well.

Three to six weeks after transfection colonies were screened by ELISA for the ability to secrete human IgG. Wells of ELISA plates (Immulon 4, Dynatech) were coated in 50 mM sodium bicarbonate/carbonate pH 9.6 with 100 ng per well of goat anti-human IgG antibodies (Harlan). Supernatant from wells containing transfected colonies was added to the wells in PBS containing 0.05% (v/v) Tween 20 (PBST) for 1 h. The plates were washed 3 times with PBST and captured human IgG was detected with 100 µl 1:2000 dilution horseradish peroxidase (HRP)-conjugated goat anti-human kappa antibodies in PBST (Harlan). After 30 min at room temperature the plates were washed 3× PBST and 100 µl OPD substrate added. Reactions were stopped after 5–10 min by the addition of 50 µl 12.5% (v/v) sulphuric acid and the A 490 nm measured.

Transfectants secreting the highest amounts of IgG were expanded for growth in glutamine-free medium in reduced FCS, in gammaglobulin-free FCS or no FCS. Cell lines were subsequently cloned by limiting dilution.

Purification of IgG

Human IgG4 antibodies were purified by protein A affinity chromatography followed by size-exclusion chromatography (SEC). Supernatant from the growth of transfected NS0 cells secreting IgG was clarified by centrifugation and filtration through a 0.22 µm membrane. A column of protein A Sepharose Fast Flow matrix (Pharmacia) was equilibrated with 0.3 M NaCl, 50 mM sodium phosphate pH 8.0 and the supernatant applied The column was then extensively washed with 50 mM sodium phosphate pH 8.0. Human IgG was eluted with 0.1 M glycine-HCl pH 3.0. Eluted fractions were neutralised with 1 M Tris HCl pH 9.0 and protein containing fractions identified by measuring the absorbance at 280 nm. Purification by SEC was on a Superdex 200 column in PBS. The IgG was finally concentrated by diafiltration against pyrogen-free PBS using a YM30 MWCO filter (Amicon).

EXAMPLE 3

Assessment of Neutralisation Properties of SL15S scFv (CAT-191) and SL15A IGG4 (CAT-192) and SL15S IGG4 (CAT-193)

The potency of neutralisation of TGFβ$_1$ was measured for SL15S scFv (Kylie scFv) and its derivatives using a radioreceptor assay and a cell proliferation assay (TF1).

Materials

[$^{125}$I]TGFβ$_1$ was supplied by Amersham (specific activity range 800–2200 Ci/mmol) Recombinant human TGFβ$_1$, β$_2$, β$_3$, latent TGFβ$_1$, GM-CSF and IL-5 were obtained from R&D Systems (Minneapolis USA). Genzyme murine mAb against TGFβ$_1$, β$_2$ and β$_3$ was obtained from Genzyme (Cambridge, Mass., USA). The TF1 cell line was supplied by Robin Thorpe (NIBSC, UK) and cultured as detailed below The A549 human lung epithelial carcinoma cell line was obtained from ATCC and grown in DMEM with 10% FCS and 2 mM glutamine. All other reagents were supplied by Sigma.

Methods

Radioreceptor Assay

A549 cells were seeded into 24-well plates at 2×10$^5$ cells per well for 24 hours in order to achieve >90% confluency. Immediately before the assay, monolayers were washed twice with buffer (1:1 DMEM:Hams-F12) and 0.5 ml assay buffer (1:1 DMEM:Hams F12+0 1% BSA) was added. Two or three-fold serial dilutions of antibodies were prepared in assay buffer and added to an equal volume of 40 pM [$^{125}$I]TGFβ$_1$ in assay buffer.

After 1 hour at room temperature, 0.5 ml of this antibody/[$^{125}$I]TGFβ$_1$ mixture was added in duplicate to the cells (already in 0.5 ml assay buffer) and incubated for 1 hour at 37° C. Final concentration of [$^{125}$I]TGFβ$_1$ was 10 pM. Controls were included as maximum binding (to cells, no antibody) and minimum binding (wells incubated with buffer but no cells) in at least triplicate.

Finally plates were washed 4× with ice-cold PBS before 0.8 ml solubilisation buffer (25 mM Tris pH 7.5, 10% glycerol, 1% Triton ×100) was added. Plates were left for at least 20 minutes on a rocking platform before the contents of each well were counted using a gamma counter.

Data were expressed after subtraction of minimum binding, as % of maximum binding.

In the study using latent TGFβ$_1$, % maximum was calculated for each set of conditions (eg in the presence of latent TGFβ$_1$, acid-activated latent TGFβ$_1$ or active TGFβ$_1$). (Lucas C et al (1991) *Meth in Enzymology* 198, 303–16)

TF1 Assay

TF1 cells were routinely grown in RPMI1640 containing 5% FCS and 2 mM glutamine (growth medium) with 2 ng/ml GM-CSF. Immediately before the experiment, cells were washed twice and resuspended at 4×10$^5$ cells/ml in fresh medium supplemented with 4 ng/ml IL-5 either with or without TGFβ$_1$, β$_2$ or β$_3$ (each at 50 pM) and 100 µl aliquots transferred to 96-well plates. scFv preparations used in this assay were FPLC-purified fractions which had had endotoxin removed.

Antibodies (two fold dilution series) were prepared in growth medium and 100 µl added to cells in duplicate. Controls were cells with TGFβ only (no antibody, maximum inhibition of growth) and cells with no TGFβ and no antibody (minimum inhibition). Cells were incubated for 48 hours at 37° C.

At the end of the assay cell number was assayed using CellTiter96 (Promega) and data expressed as % neutralisation i.e $$\% \text{ neutralisation} = \frac{(\text{test value} - \text{maximum inhibition})}{(\text{minimum inhibition} - \text{maximum inhibition})} \times 100$$

In the study of latent TGFβ$_1$, data were expressed as % of control (growth in the absence of TGFβ$_1$) as the amount of active TGFβ$_1$ in each test condition varied.
(Randall L A et al (1993) *J Immunol Meth* 164, 61–7)

Production of Antibodies

ScFv antibodies and IgG4 antibodies were prepared and purified as described above.

Results

Potency of SL15S scFv (CAT-191) and SL15A IgG4 (CAT-192) in a bioassay (TF1 Assay)

The ability of SL15S scFv (CAT-191) to recognise TGFβ$_1$ but not TGFβ$_2$ or β$_3$ in the TF1 assay was investigated.

SL15S scFV (also known as Kylie scFV) neutralised the growth inhibition induced by TGFβ$_2$ but not that induced by TGFβ$_2$ or TGFβ$_3$ (FIG. 1) As a control, a monoclonal antibody, Genzyme Mab 1.D.11.16, was used (Genzyme, Dasch, J. R., et al, *J. Immunol.*, 142, 1536–1541, 1989), which neutralises $TGF\beta_1$, $TGF\beta_2$ and $TGF\beta_3$. Mab 1.D.11.16 has been shown to be effective in models of lung fibrosis, radiation induced fibrosis (Barcellos-Hoff, U.S. Pat. No. 5,616,561, 1997) and rheumatoid arthritis (Wahl et al, J. Exp. Medicine, 177, 225–230, 1993). SL15S scFv shows comparable potency to the Genzyme Mab 1.D.11 16 control against $TGF\beta_1$.

Figure 2:
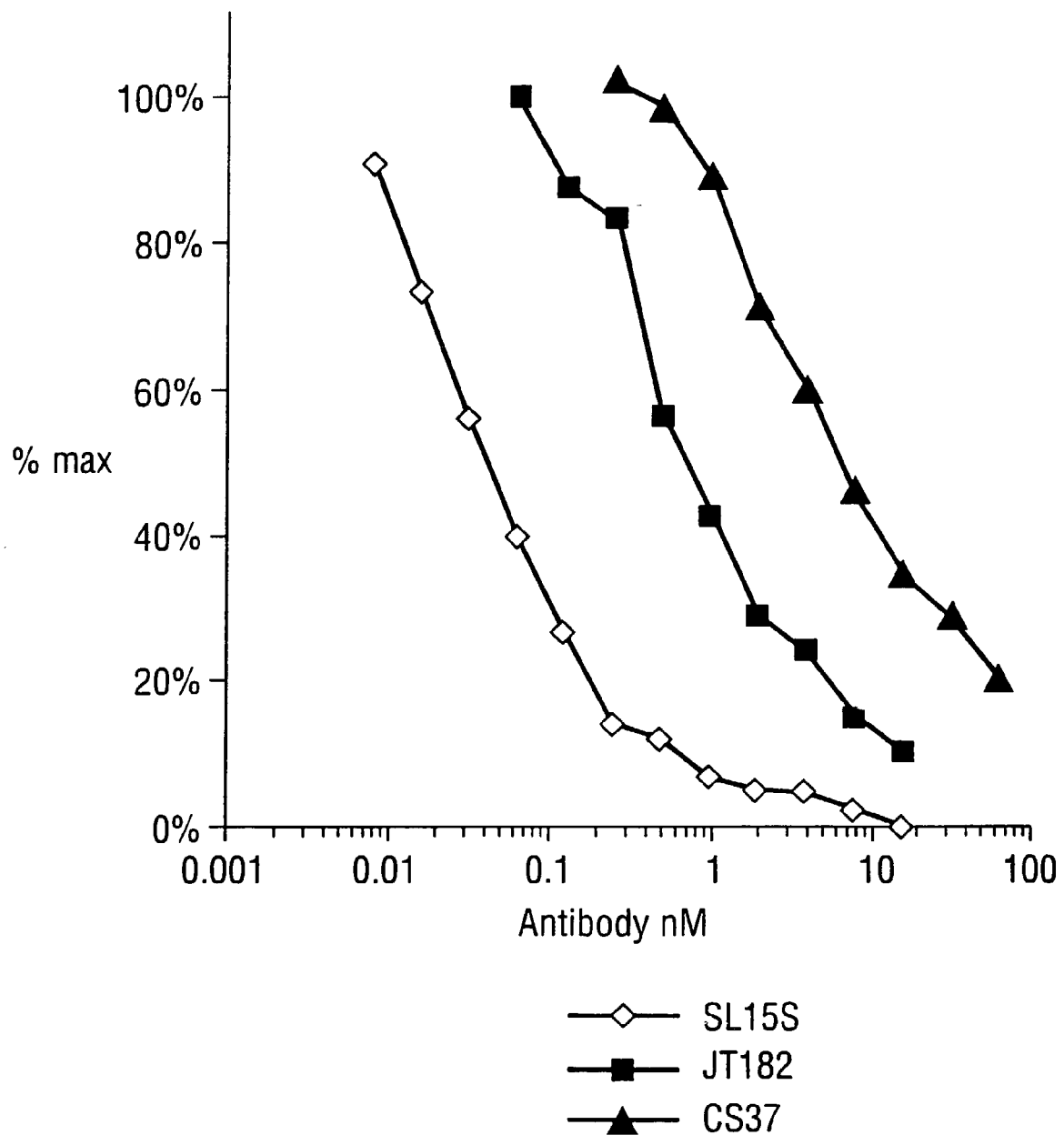
FIG. 2: Inhibition of [$^{125}$I]$TGF\beta_1$ binding to A549 cells by anti-$TGF\beta_1$ scFv ScFv preparations of SL15S, JT183 and CS37 were titrated 2-fold and tested for their ability to inhibit [$^{125}$I]TGFβ$_1$ binding to A549 cells. SL15S and JT182 were used as his-preps, CS37 was fplc-purified.
Figure 3:
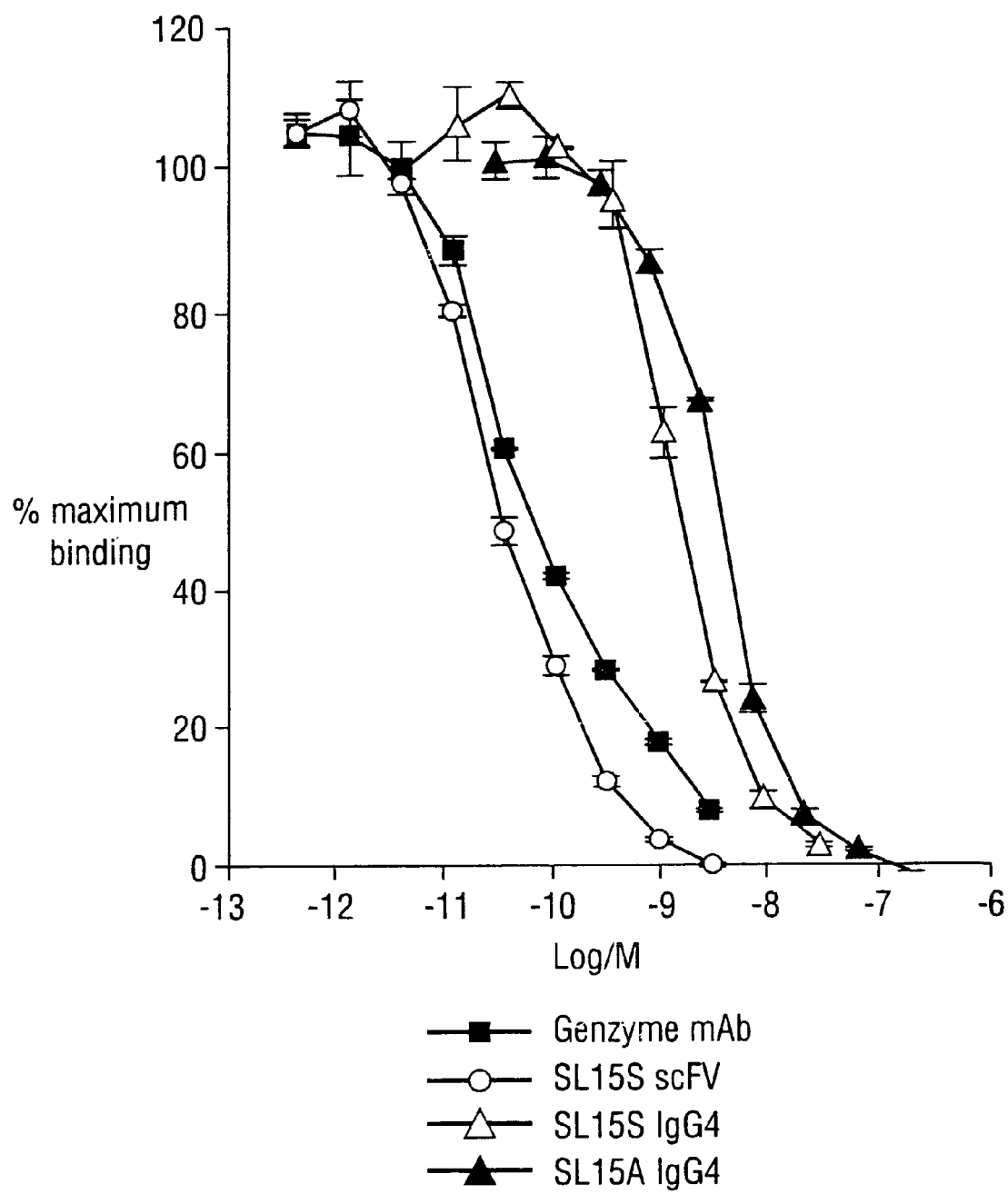
FIG. 3: Inhibition of [$^{125}$I]TGFβ$_1$ binding to A549 cells by anti-TGFβ$_1$ antibodies. SL15S scFv, SL15S IgG4 and SL15A IgG4 were compared with Genzyme mAb in their ability to inhibit [$^{125}$I]TGFβ$_1$ binding to A549 cells Data are the average of 3 experiments, using a three-fold dilution series.
Figure 8:
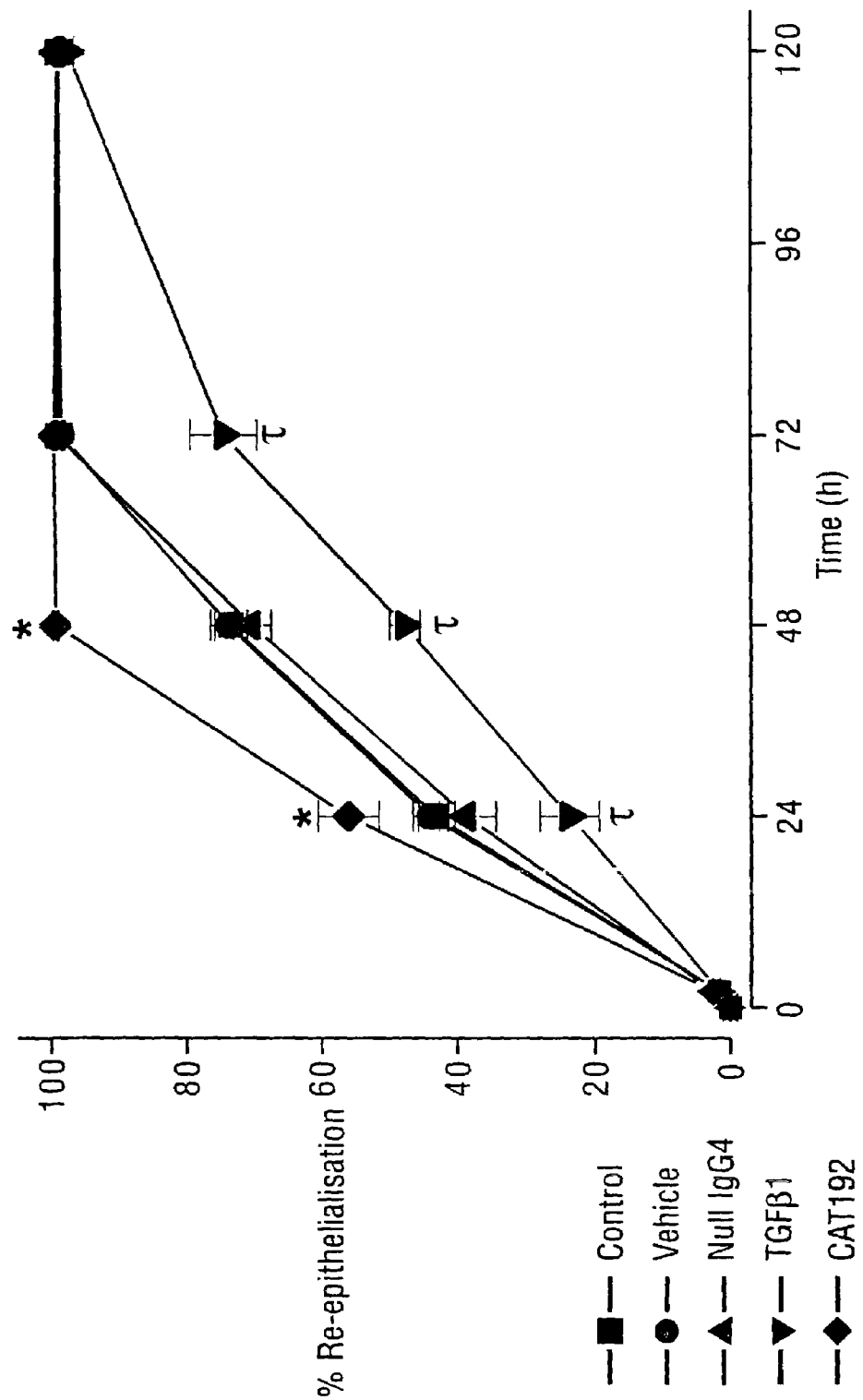
FIG. 8. The effect of CAT192 on corneal re-epithelialisation was investigated following an excisional trephine wound of bovine isolated cornea in the air interface organ culture model. Bovine cornea were treated with 100 μl of either serum free Medium 199 (control) or medium containing vehicle (for antibody and TGFβ$_1$). Null isotype-matched antibody (10 μg), TGFβ$_1$ (1ng) or CAT192 (10 μg) were administered immediately after wounding and at 12 h intervals thereafter. CAT192 caused a significant increase in rate of re-epithelialisation of wounded bovine cornea whereas TGFβ$_1$ caused a significant decrease in this variable. Data are expressed as percentage re-epithelialisation of the corneal wound. Each point represents the mean value and the vertical bars show s.e.mean of 8 cornea per point. The effect of the different treatments were compared at each time point using repeated measures ANOVA with Bonferroni test *P<0.01 compared to the null antibody treatment group; t P<0.01 compared to the vehicle treated group.
Figure 9:
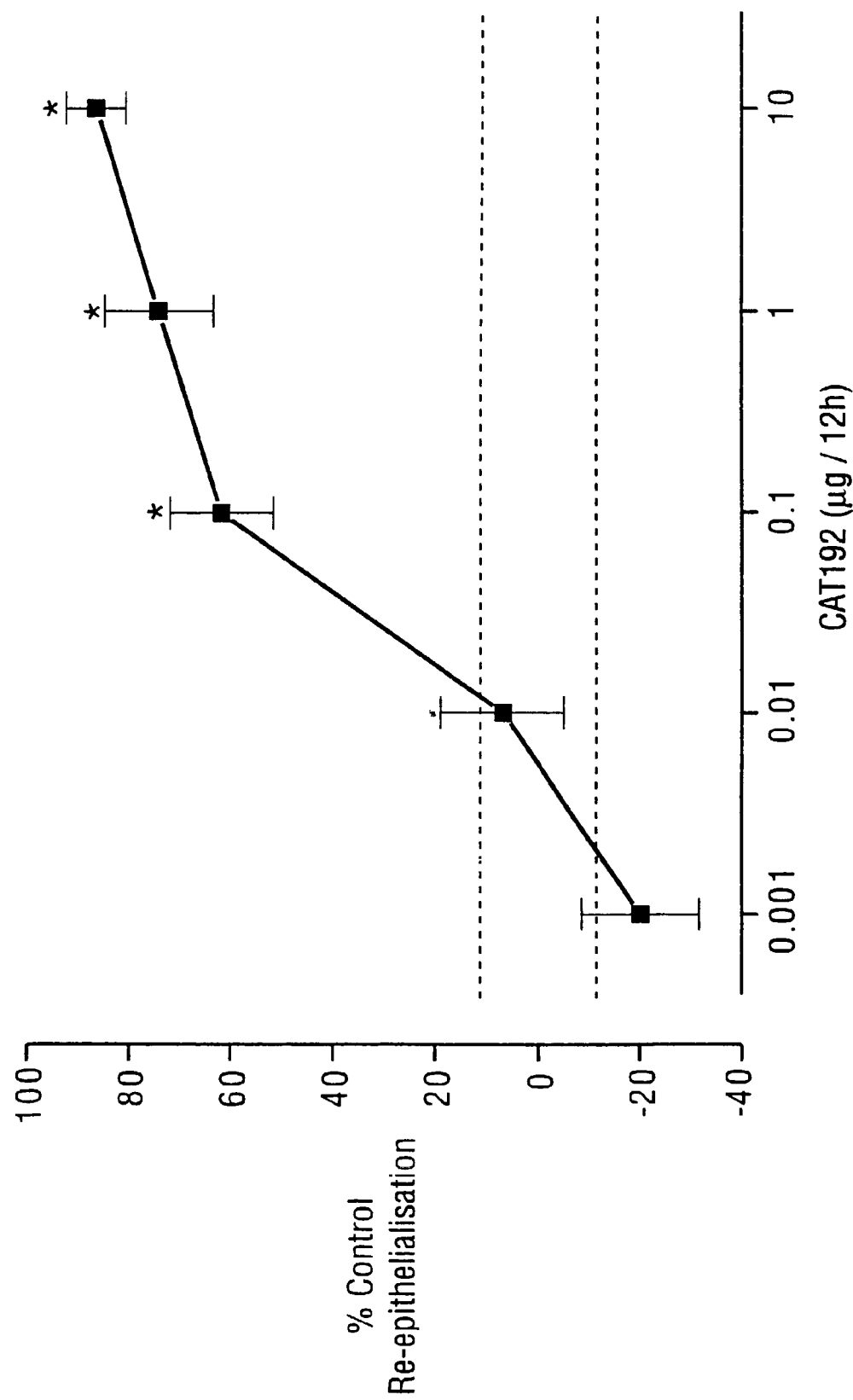
FIG. 9: The effect of CAT192 on corneal re-epithelialisation was investigated following an excisional trephine wound of bovine isolated cornea in the air interface organ culture model. CAT192 (0.001–10 μg) was administered immediately after wounding and at 12 h intervals thereafter. CAT192 caused a significant dose-related increase in re-epithelialisation of wounded bovine cornea. The EC50 for CAT192 was between 0.01 and 0.1 μg. Data are expressed as the percentage change in re-epithelialisation of the vehicle treated control group. The dotted lines show the s.e. mean values of the vehicle control group. Each point represents the mean value and and the vertical bars show s.e mean of 6 cornea per point The effect of the different doses of CAT192 were compared to control treatment using one way ANOVA and Dunnett's test; *P<0.01.

The activity of SL15A IgG4 (CAT-192; also termed Kylie IgG4) was also shown in the TF1 assay (FIG. 5b) in the study using latent $TGF\beta_1$ Potency of SL15S scFv (CAT-191), SL15A IgG4 (CAT-192) and SL15S IgG4 (CAT-193) in the Radioreceptor Assay The ability of SL15S scFv to recognise $TGF\beta_1$ and neutralise binding of $TGF\beta_1$ to A549 cells was measured in the radioreceptor assay In a comparision of his-preps of scFv, SL15S (Kylie) was compared to the parental antibodies CS37 and JT182 (FIG. 2) and was found to be 100- to 150-fold and 10-fold more active. SL15 was reformatted as IgG in two forms, SL15A IgG4 (CAT-192) and SL15S IgG4 (CAT-193). Purified preparations of SL15S scFv, SL15A IgG4, SL15S IgG4 and Mab 1D.11.16 (Genzyme mAb) were also analysed (FIG. 3).

SL15S scFv has comparable potency to the Genzyme Mab 1. D.11.16, which is effective in animal models. In summary, SL15S scFv is a highly potent, neutralising antibody for $TGF\beta_1$, with $IC_{50}$ values in the range 0.03 to 0 1 nM

EXAMPLE 4

Binding of the Antibody SL15S scFv (CAT-191) and SL15A IGG4 (CAT-192) to Active and Latent $TGF\beta_1$ The experiments described in this example demonstrated that SL15S scFv and SL15A IgG4 bind to and neutralise active, but not latent, $TGF\beta_1$.

Latent $TGF\beta_1$ is the biologically inactive form in which $TGF\beta_1$ is secreted from cells, and is composed of a latency associated peptide dimer (consisting of two 249 amino acid monomers) and a mature $TGF\beta_1$ dimer (consisting of two 112 amino acid monomers). Latent $TGF\beta_1$ is not recognised by cell surface $TGF\beta$ receptors. Active $TGF\beta_1$ is thought to be released by the action of proteases in vivo which can be mimicked by acidification in vitro.

Latent $TGF\beta_1$, has a reported ED50 of 0 43 nM and 2 pM before and after acidification respectively, as assayed in a proliferation assay Active $TGF\beta_1$ has a reported ED50 in a proliferation assay of approximately 2 pM Presumably the effect of latent $TGF\beta_1$ before acidification is due to the presence of some active $TGF\beta_1$. This residual activity must be considered on interpretation of the results.

The potency of SL15S scFv and SL15A IgG4 was tested using the radioreceptor assay and TF1 proliferation assay in the presence of varying amounts of latent $TGF\beta_1$, acid-activated $TGF\beta_1$ and active $TGF\beta_1$. If the antibodies recognise latent $TGF\beta_1$, their potency should be reduced. Interpretation of both assays is complicated by the fact that any active $TGF\beta_1$ present in the latent preparation will compete with $[^{125}I]TGF\beta_1$ for binding and have biological activity on the cells.

Latent $TGF\beta_1$ was acid-activated by the addition of 2 μl 0.5M HCl to 1 ml latent $TGF\beta_1$ for 15 min at room temperature then neutralised with 43 μl 0.05 M NaOH/0 01 M Hepes.

Results show that in the radioreceptor assay there is no significant effect of latent $TGF\beta_1$ (0.1 nM) on the potency of SL15S scFv (Kylie scFv) or SL15A IgG4 (Kylie IgG), whereas acid-activation of the latent $TGF\beta_1$, or an equivalent concentration of active $TGF\beta_1$ reduces the ability of the antibody to neutralise $[^{125}I]TGF\beta_1$ binding (FIG. 4).

The TF1 proliferation assay was very sensitive to the activity of the active $TGF\beta_1$ in the latent $TGF\beta_1$ preparation. Nevertheless, the SL15S scFv or SL15A IgG4 were found to be able to neutralise the small proportion of active $TGF\beta_1$ of the latent preparation and when the latent $TGF\beta_1$ is acid-activated neutralise this effectively (FIG. 5).

Therefore, SL15, in the scFv or IgG format, binds and neutralises only active but not latent $TGF\beta_1$ as measured by both the radioreceptor and the TF1 neutralisation assay.

EXAMPLE 5

Epitope Mapping of the Antibodies SL15S scFv and CS37scFv

In this example the epitope on $TGF\beta_1$ to which the antibodies CS37 and SL15S binds was determined.

$TGF\beta_1$ and $TGF\beta_2$ have similar structures but differ in their binding affinity for the $TGF\beta$ type II receptor and their potency in a number of biological assays (O. G. Ottmann & L. M *Pelus J. Immunol.* 140: 2661–2665, 1988; J. R Merwin et al, *Am. J. Pathol.*, 138: 37–51, 1991; K. C. Flanders et al., *Development* 113: 183–191, 1991; L. Suardet et al *Cancer Res.* 52: 3705–3712, 1992). Qian et al (*J. Biol. Chem.* 271: 30656–30662, 1996) have taken advantage of the differences in affinity to identify the key residues involved in the high affinity binding of $TGF\beta_1$ to the type II receptor. This has been done by making a series of chimeric molecules between $TGF\beta_1$ and $TGF\beta_2$ and identifying those species which retain high affinity receptor binding in vitro (Qian et al, supra) and in vivo (J. K. Burmester et al *Growth Factors* 15: 231–242, 1998). In this way, the C terminal region encompassed by residues 83–112 of $TGF\beta_1$ was identified as sufficient to retain efficient receptor binding.

Comparison of the sequences of $TGF\beta_1$ and $TGF\beta_2$ identified several differences including a loop consisting of residues 92–98, which includes 4 amino acid differences between $TGF\beta_1$ and $TGF\beta_2$. When these residues from $TGF\beta_2$ were introduced into a $TGF\beta_1$ backbone, receptor binding was greatly reduced, identifying these as key residues in the interaction of $TGF\beta_1$ with the type II receptor.

The chimeric molecules were used in a similar way to map the binding site of CS37 and SL15S scFv (CAT-191) on $TGF\beta_1$. $TGF\beta_1/\beta_2$ (83–112) corresponds to the N-terminal and central region of $TGF\beta_1$ from residues 1–82, fused with the C-terminal region of $TGF\beta_2$ from residues 83–112. $TGF\beta_2/\beta1$ 83–112 corresponds to the N-terminal and central region of $TGF\beta_2$ from residues 1–82, fused with the C-terminal region of $TGF\beta_1$ from residues 83–112. Finally, $TGF\beta_1-\beta_2$ (40–112) corresponds to the N-terminal region of $TGF\beta_1$ from residues 1–39, and the central and C-terminal region of $TGF\beta_2$ from residues 40–112. These are referred to hereafter as 1-1-2, 2-2-1 and 1-2-2 respectively to reflect the relative composition of the isoforms These three molecules along with $TGF\beta_1$ and $TGF\beta_2$ were profiled for inhibition of binding of SL15S scFv and CS37 scFv to immobilized $TGF\beta_1$ as follows Phage displaying SL15S scFv or CS37 scFv were prepared from clones in pCANTAB6, by M13K07 superinfection. Phage were PEG precipitated and resuspended in PBS containing 2% Marvel. Phage (2.5 to 5×10$^{10}$ in 50 µl) was added for 30 minutes to a preblocked ELISA plate coated with TGFβ$_1$ at 0.5 µg/ml For inhibition analysis, the same concentration of phage was used and a dilution series of TGFβ concentrations set up for each of the TGFβ chimeric molecules described above (Gift from J. Burmester, National Institutes of Health) and the TGFβ$_1$ and 2 isoforms.

These were incubated overnight at 4° C. before adding to the ELISA plate. Phage that bound specifically to the antigen coated plate were detected using a sheep anti-fd antiserum (Pharmacia), followed by alkaline phosphatase conjugated anti-sheep immunoglobulin (Sigma) and p-nitrophenyl phosphate (pNPP) substrate (Sigma).

The uninhibited value (i e 0 nM) for Kylie was 167 (Average of 3 readings) and for CS37 was 1.216 (Average of 7 readings).

Figure 6:
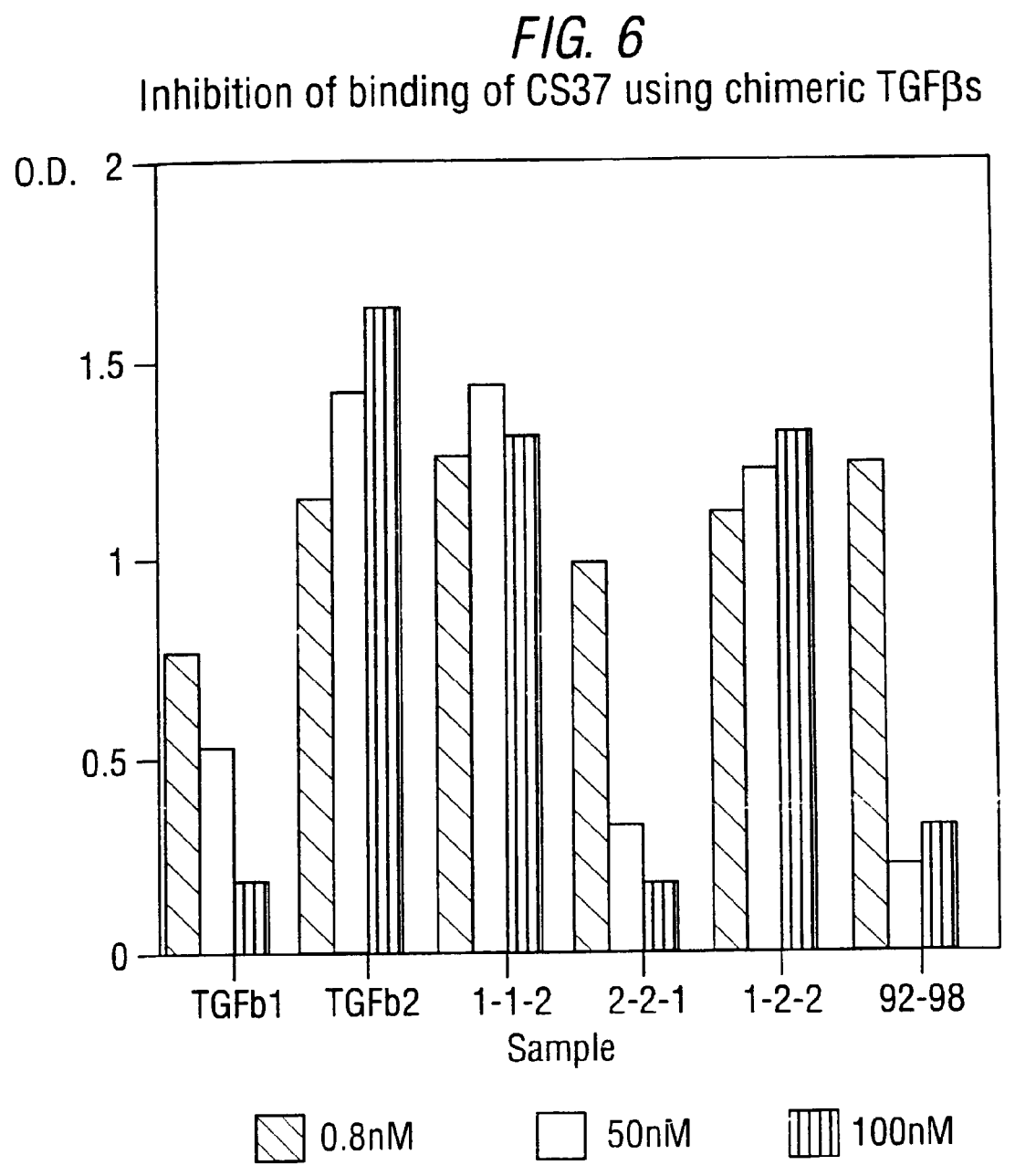

The result shown in FIGS. 6 and 7 indicates that the epitopes recognised both by CS37 scFv and SL1SS scFv reside between residues 83–112 of TGFβ$_1$. Furthermore, the mutant molecule TGFβ$_1$–β$_2$ (92–98) which comprises TGFβ$_1$ with the TGFβ$_2$ sequence from residues 92–98 also inhibits CS37 and SL15S scFv binding to TGFβ$_1$ but with reduced effect, especially for SL15S scFv. This demonstrates that at least part of the epitope recognised by these antibodies resides within the region 92–98, (which has four residues, at positions 92, 94, 95 and 98, which differ between $TGF\beta_1$ and $TGF\beta_2$).

EXAMPLE 6

Acceleration of Corneal Epithelial Wound Healing in the Presence of the Anti-TGFb1 Monoclonal Antibody SL15A IgG4 (CAT-192)

TGFβhas been implicated in the modulation of wound healing (both ocular and dermal) and has been shown to inhibit the rate of corneal re-epithelialisation. Here the effect of topical application of SL15A IgG4 (CAT-192) on the rate of corneal epithelial wound healing was assessed using an organ culture model (D M Foreman et al, *Exp. Eye Res.* 62: 555–564, 1996).

Excisional trephine wounds (5 mm diameter, 250 μm depth) were created on bovine corneas. Corneal scleral rings were maintained in a serum-free, air-interface organ culture system for up to 96 hr At time of wounding, and twice daily thereafter, 100 μl of serum-free T8 medium was added dropwise to the epithelial surface and limbus, containing (i) 10 ng/ml $TGF\beta_1$, (ii) 100 μg/ml anti-$TGF\beta_1$ mAb, (iii) a combination of (i) and (ii), (iv) 100 μg/ml null antibody (2G6 IgG4), (v) 100 μg/ml antibody diluent; or (vi) no additions (n=9 for each group) Re-epithelialisation was assessed using an image analysis system and expressed as percentage of the original wound area covered by epithelium.

Control corneas that received medium alone, null antibody or antibody diluent demonstrated complete re-epithelialisation by 72 hr. Treatment with 100 μg/ml of anti-$TGF\beta_1$ mAb increased the rate of re-epithelialisation such that corneas were completely re-epithelialised by 48 hours (FIG. 8). Corneas treated with 10 ng/ml $TGF\beta_1$ demonstrated delayed re-epithelialisation by 24 hours and this inhibitory effect was abolished by anti-$TGF\beta_1$ mAb (FIG. 9). All differences quoted are significant (p<0 05). Linear regression was performed on the data points between 2 and 48 h (see FIG. 8) to determine the rate of re-epithelialisation. CAT192 caused a significant increase in this variable (Table 3). Histological analysis supported the image analysis results and confirmed that addition of anti-$TGF\beta_1$ mAb did not adversely affect corneal architecture.

TABLE 3

The effect of CAT192 or $TGF\beta_1$ on the rate of re-epithelialisation of bovine isolated cornea in air interface organ culture following excisional trephine wound.

| Treatment | Rate of Re-epithelialisation ($\% \ h^{-1}$) | n |
|---|---|---|
| Medium 199 (100 μl) | 1.56 ± 0.07 | 8 |
| Vehicle (100 μl) | 1.57 ± 0.08 | 8 |
| Null antibodyIgG4 (10 μl) | 1.48 ± 0.09 | 8 |
| $TGF\beta_1$ (1 ng) | 1.01 ± 0.09τ | 8 |
| CAT192 (10 μl) | 2.11 ± 0.09* | 8 |

Table 3 legend: Bovine cornea were treated with 100 μl of either serum free Medium 199 (control) or medium containing vehicle (for antibody and $TGF\beta_1$) null IgG4 isotope-matched antibody, $TGF\beta_1$ or CAT192 immediately after wounding and at 12 h intervals thereafter. Linear regression was performed on the data points between 2 and 48 h (see FIG. 8) to determine the rate of re-epithelialisation. CAT192 caused a significant increase in the rate of re-epithelialisation of wounded bovine cornea whereas $TGF\beta_1$ caused a significant decrease in this variable. Values shown are the mean value and the s.e. mean. The effect of the different treatments was compared using one way ANOVA with Tukey test. *P < 0.01 compared to the null antibody treatment group, ᵀP0.01 compared to the vehicle treated group.

These results confirm the important role of endogenous $TGF\beta_1$ in corneal epithelial repair and provide indication that the topical application of the anti-$TGF\beta_1$ mAb SL15A IgG4 (CAT-192) may be used to promote improved wound healing in vivo.

We claim:

1. Isolated nucleic acid encoding a specific binding member that binds TGFβ$_1$, wherein said specific binding member comprises an antigen binding domain that comprises an antibody VH domain and an antibody VL domain, wherein the antibody VH domain consists of the amino acid sequence of SEQ ID NO: 4 and the antibody VL domain consists of the amino acid sequence of SEQ ID NO: 6 or SEQ ID NO: 8.

2. The isolated nucleic acid of claim 1 wherein the antibody VL domain consists of the amino acid sequence of SEQ ID NO: 6.

3. Isolated nucleic acid encoding a specific binding member that binds TGFβ$_1$, wherein said specific binding member comprises an antigen binding domain that comprises an antibody VH domain and antibody VL domain, wherein the antibody VH domain consists of the amino acid sequence of SEQ ID NO: 10 and the antibody VL domain consists of the amino acid sequence of SEQ ID NO: 6 or SEQ ID NO: 8.

4. The isolated nucleic acid of claim 1, 2 or 3 wherein the specific binding member is in the form of a single chain Fv (scFv).

5. The isolated nucleic acid of claim 1, 2 or 3 wherein the specific binding member is in the form of an IgG.

6. The isolated nucleic acid of claim 5 wherein said IgG is an IgG1 or IgG4.

7. A nucleic acid construct comprising the nucleic acid of claim 1, 2 or 3.

8. A recombinant host cell comprising the nucleic acid construct of claim 7.

9. A method of preparing a specific binding member capable of binding TGFβ$_1$, said method comprising expressing the nucleic acid of claim 1, 2 or 3 in a host cell under conditions to provide for expression of said nucleic acid, followed by recovery of said specific binding member.

* * * * *

SEQUENCE LISTING

```
<160> NUMBER OF SEQ ID NOS: 25

<210> SEQ ID NO 1
<211> LENGTH: 369
<212> TYPE: DNA
<213> ORGANISM: Homo sapiens

<400> SEQUENCE: 1
caggtgcagc tggtgcagtc tgggggaggc gtggtccagc ctgggaggtc cctgagactc      60
tcctgtgcag cctctggatt caccttcagt agctatggca tgcactgggt ccgccaggct     120
```

```
ccaggcaagg ggctggagtg ggtggcagtt atatcatatg atggaagtat taaatactat    180
gcagactccg tgaagggccg attcaccatc tccagagaca attccaagaa cacgctgtat    240
ctgcaaatga acagcctgag agctgaggac acggctgtgt attactgtgc gcgaactggt    300
gaatatagtg gctacgatac gagtggtgtg gagctctggg gcaagggac cacggtcacc    360 gtctcctca                                                           369
```

<210> SEQ ID NO 2
<211> LENGTH: 123
<212> TYPE: PRT
<213> ORGANISM: Homo sapiens
<400> SEQUENCE: 2

```
Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Ser Gly Val Glu Leu
           100                 105                 110

Trp Gly Gln Gly Thr Thr Val Thr Val Ser Ser
        115                 120
```

<210> SEQ ID NO 3
<211> LENGTH: 369
<212> TYPE: DNA
<213> ORGANISM: Homo sapiens
<400> SEQUENCE: 3

```
gaggtccagc tggtggagtc tgggggaggc gtggtccagc ctggagtc cctgagactc    60 tcctgtgcag cctctggatt caccttcagt agctatggca tgcactgggt ccgccaggct    120
ccaggcaagg agctggagtg ggtggcagtt atatcatatg atggaagtat taaatactat    180
gcagactccg tgaagggccg attcaccatc tccagagaca attccaagaa cacgctgtat    240
ctgcaaatga acagcctgag agctgaggac acggctgtgt attactgtgc gcgaactggt    300
gaatatagtg gctacgatac ggaccccag tactcctggg gcaagggac cacggtcacc    360 gtctcctca                                                           369
```

<210> SEQ ID NO 4
<211> LENGTH: 123
<212> TYPE: PRT
<213> ORGANISM: Homo sapiens
<400> SEQUENCE: 4

```
Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Glu Leu Glu Trp Val
             35                  40                  45

Ala Val Ile Ser Tyr Asp Gly Ser Ile Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Thr Gly Glu Tyr Ser Gly Tyr Asp Thr Asp Pro Gln Tyr Ser
             100                 105                 110

Trp Gly Gln Gly Thr Thr Val Thr Val Ser Ser
         115                 120

<210> SEQ ID NO 5
<211> LENGTH: 321
<212> TYPE: DNA
<213> ORGANISM: Homo sapiens

<400> SEQUENCE: 5
gaaattgtgc tgactcagtc tccatcctcc ctgtctgcat ctgtaggaga cagagtcacc     60
atcacttgcc gggcaagtca gggcattgga gatgatttgg ctggtatca gcagaagcca    120 gggaaagccc ctatcctcct gatctatggt acatccactt tacaaagtgg ggtcccgtca    180
aggttcagcg gcagtggatc tggcacagat ttcactctca ccatcaacag cctgcagcct    240
gaagattttg caacttatta ctgtctacaa gattccaatt acccgctcac tttcggcgga    300
gggacacgac tggagattaa a                                              321

<210> SEQ ID NO 6
<211> LENGTH: 107
<212> TYPE: PRT
<213> ORGANISM: Homo sapiens

<400> SEQUENCE: 6

Glu Ile Val Leu Thr Gln Ser Pro Ser Ser Leu Ser Ala Ser Val Gly
  1               5                  10                  15

Asp Arg Val Thr Ile Thr Cys Arg Ala Ser Gln Gly Ile Gly Asp Asp
             20                  25                  30

Leu Gly Trp Tyr Gln Gln Lys Pro Gly Lys Ala Pro Ile Leu Leu Ile
         35                  40                  45

Tyr Gly Thr Ser Thr Leu Gln Ser Gly Val Pro Ser Arg Phe Ser Gly
 50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Leu Gln Asp Ser Asn Tyr Pro Leu
                 85                  90                  95

Thr Phe Gly Gly Gly Thr Arg Leu Glu Ile Lys
             100                 105

<210> SEQ ID NO 7
<211> LENGTH: 321
<212> TYPE: DNA
<213> ORGANISM: Homo sapiens

<400> SEQUENCE: 7
gaaattgtgc tgactcagtc tccatcctcc ctgtctgcat ctgtaggaga cagagtcacc     60
atcacttgcc ggtcaagtca gggcattgga gatgatttgg ctggtatca gcagaagcca    120
```

```
gggaaagccc ctatcctcct gatctatggt acatccactt tacaaagtgg ggtcccgtca        180
aggttcagcg gcagtggatc tggcacagat ttcactctca ccatcaacag cctgcagcct        240
gaagattttg caacttatta ctgtctacaa gattccaatt acccgctcac tttcggcgga        300
gggacacgac tggagattaa a                                                  321
```

<210> SEQ ID NO 8
<211> LENGTH: 107
<212> TYPE: PRT
<213> ORGANISM: Homo sapiens

<400> SEQUENCE: 8

```
Glu Ile Val Leu Thr Gln Ser Pro Ser Ser Leu Ser Ala Ser Val Gly
 1               5                  10                  15

Asp Arg Val Thr Ile Thr Cys Arg Ser Ser Gln Gly Ile Gly Asp Asp
                20                  25                  30

Leu Gly Trp Tyr Gln Gln Lys Pro Gly Lys Ala Pro Ile Leu Leu Ile
            35                  40                  45

Tyr Gly Thr Ser Thr Leu Gln Ser Gly Val Pro Ser Arg Phe Ser Gly
50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys
            100                 105
```

<210> SEQ ID NO 9
<211> LENGTH: 369
<212> TYPE: DNA
<213> ORGANISM: Homo sapiens

<400> SEQUENCE: 9

```
caggtgcagc tggtggagtc tgggggaggc gtggtccagc ctgggaggtc cctgagactc         60
tcctgtgcag cctctggatt caccttcagt agctatggca tgcactgggt ccgccaggct        120
ccaggcaagg agctggagtg ggtggcagtt atatcatatg atggaagtat taaatactat        180
gcagactccg tgaagggccg attcaccatc tccagagaca attccaagaa cacgctgtat        240
ctgcaaatga acagcctgag agctgaggac acggctgtgt attactgtgc gcgaactggt        300
gaatatagtg gctacgatac gcccgcctcg ccggactggg gcaagggac cacggtcacc         360 gtctcctca                                                                369
```

<210> SEQ ID NO 10
<211> LENGTH: 123
<212> TYPE: PRT
<213> ORGANISM: Homo sapiens

<400> SEQUENCE: 10

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Glu Leu Glu Trp Val
            35                  40                  45

Ala Val Ile Ser Tyr Asp Gly Ser Ile Lys Tyr Tyr Ala Asp Ser Val
50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Thr Gly Glu Tyr Ser Gly Tyr Asp Thr Pro Ala Ser Pro Asp
            100                 105                 110

Trp Gly Gln Gly Thr Thr Val Thr Val Ser Ser
        115                 120
```

<210> SEQ ID NO 11
<211> LENGTH: 5
<212> TYPE: PRT
<213> ORGANISM: Homo sapiens

<400> SEQUENCE: 11

```
Ser Tyr Gly Met His
 1               5
```

<210> SEQ ID NO 12
<211> LENGTH: 17
<212> TYPE: PRT
<213> ORGANISM: Homo sapiens

<400> SEQUENCE: 12

```
Val Ile Ser Tyr Asp Gly Ser Ile Lys Tyr Tyr Ala Asp Ser Val Lys
 1               5                  10                  15

Gly
```

<210> SEQ ID NO 13
<211> LENGTH: 14
<212> TYPE: PRT
<213> ORGANISM: Homo sapiens

<400> SEQUENCE: 13

```
Thr Gly Glu Tyr Ser Gly Tyr Asp Thr Asp Pro Gln Tyr Ser
 1               5                  10
```

<210> SEQ ID NO 14
<211> LENGTH: 14
<212> TYPE: PRT
<213> ORGANISM: Homo sapiens

<400> SEQUENCE: 14

```
Thr Gly Glu Tyr Ser Gly Tyr Asp Thr Ser Gly Val Glu Leu
 1               5                  10
```

<210> SEQ ID NO 15
<211> LENGTH: 14
<212> TYPE: PRT
<213> ORGANISM: Homo sapiens

<400> SEQUENCE: 15

```
Thr Gly Glu Tyr Ser Gly Tyr Asp Thr Pro Ala Ser Pro Asp
 1               5                  10
```

<210> SEQ ID NO 16
<211> LENGTH: 11
<212> TYPE: PRT
<213> ORGANISM: Homo sapiens

<400> SEQUENCE: 16

```
Arg Ala Ser Gln Gly Ile Gly Asp Asp Leu Gly
 1               5                  10
```

<210> SEQ ID NO 17
<211> LENGTH: 7
<212> TYPE: PRT
<213> ORGANISM: Homo sapiens

<400> SEQUENCE: 17

Gly Thr Ser Thr Leu Gln Ser
 1               5

<210> SEQ ID NO 18
<211> LENGTH: 9
<212> TYPE: PRT
<213> ORGANISM: Homo sapiens

<400> SEQUENCE: 18

Leu Gln Asp Ser Asn Tyr Pro Leu Thr
 1               5

<210> SEQ ID NO 19
<211> LENGTH: 11
<212> TYPE: PRT
<213> ORGANISM: Homo sapiens

<400> SEQUENCE: 19

Arg Ser Ser Gln Gly Ile Gly Asp Asp Leu Gly
 1               5                  10

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
ctaagcttac tgagcacaca ggacctcacc                                    30

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
aattttcgaa ctacagttac tgagcacaca ggacc                              35

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
atgggccctt ggtggaagct gaggagacgg tgaccgtggt cccttg                  46

<210> SEQ ID NO 23
<211> LENGTH: 53
<212> TYPE: DNA
<213> ORGANISM: Artificial Sequence
<220> FEATURE:
<223> OTHER INFORMATION: Description of Artificial Sequence:
      Oligonucleotide

```
<400> SEQUENCE: 23
ttggatatct ctccacaggt gtccactccg aaattgtgct gactcagtct cca        53

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
ctaccgtacg tttaatctcc agtcgtgtcc ctccgccgaa                       40

<210> SEQ ID NO 25
<211> LENGTH: 52
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
ttggatatct ctccacaggt gtccactccg aggtgcagct ggtggagtct gg         52
```